US010806477B2

(12) United States Patent
Goldfarb et al.

(10) Patent No.: US 10,806,477 B2
(45) Date of Patent: *Oct. 20, 2020

(54) SYSTEMS AND METHODS FOR TRANSNASAL DILATION OF PASSAGEWAYS IN THE EAR, NOSE OR THROAT

(71) Applicant: Acclarent, Inc., Irvine, CA (US)

(72) Inventors: Eric Goldfarb, Belmont, CA (US); John Y. Chang, Los Altos, CA (US); William M. Facteau, Altherton, CA (US); Sivette Lam, Milpitas, CA (US); Hung V. Ha, San Jose, CA (US); Isaac J. Kim, San Jose, CA (US); Ketan P. Muni, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 211 days.

This patent is subject to a terminal disclaimer.

(21) Appl. No.: 16/106,653

(22) Filed: Aug. 21, 2018

(65) Prior Publication Data

US 2019/0117245 A1    Apr. 25, 2019

Related U.S. Application Data

(60) Continuation of application No. 15/187,938, filed on Jun. 21, 2016, now Pat. No. 10,098,652, which is a
(Continued)

(51) Int. Cl.
*A61B 17/24* (2006.01)
*A61M 25/00* (2006.01)
(Continued)

(52) U.S. Cl.
CPC .............. *A61B 17/24* (2013.01); *A61B 6/12* (2013.01); *A61B 6/487* (2013.01);
(Continued)

(58) Field of Classification Search
None
See application file for complete search history.

(56) References Cited

U.S. PATENT DOCUMENTS

| 446,173 A | 2/1891 | Hancock |
| 504,424 A | 9/1893 | De Pezzer |
| (Continued) | | |

FOREIGN PATENT DOCUMENTS

| CA | 2013323 | 9/1990 |
| CH | 668188 | 12/1988 |
| (Continued) | | |

OTHER PUBLICATIONS

Argon Medical. Maxxim Medical. Ad for Sniper EliteTM Hydrophilic Ni—Ti Alloy Guidewire (2001).
(Continued)

*Primary Examiner* — Scott J Medway
(74) *Attorney, Agent, or Firm* — Frost Brown Todd LLC

(57) ABSTRACT

A dilation catheter device and system for dilating an opening in a paranasal sinus and/or other passageways within the ear, nose or throat is disclosed. A dilation catheter device and system is constructed in a manner that facilitates ease of use by the operator and, in at least some cases, allows the dilation procedure to be performed by a single operator. Additionally, the dilation catheter device and system may be useable in conjunction with an endoscope and/or a fluoroscope to provide for easy manipulation and positioning of the devices and real time visualization of the entire procedure or selected portions thereof. In some embodiments, shaft markers are disposed on a shaft of the dilation catheter and have a light color to contrast with a dark color of the dilation catheter shaft. The high contrast between the markers and catheter shaft allows for easy viewing of the markers in low light and operation conditions.

20 Claims, 10 Drawing Sheets

Related U.S. Application Data division of application No. 12/496,226, filed on Jul. 1, 2009, now Pat. No. 9,399,121, which is a continuation-in-part of application No. 11/789,704, filed on Apr. 24, 2007, now Pat. No. 8,747,389, which is a continuation-in-part of application No. 11/355,512, filed on Feb. 16, 2006, now Pat. No. 8,894,614, which is a continuation-in-part of application No. 11/150,847, filed on Jun. 10, 2005, now Pat. No. 7,803,150, which is a continuation-in-part of application No. 10/944,270, filed on Sep. 17, 2004, now abandoned, which is a continuation-in-part of application No. 10/829,917, filed on Apr. 21, 2004, now Pat. No. 7,654,997.

(51) Int. Cl.
*A61M 25/10* (2013.01)
*A61M 29/02* (2006.01)
*A61B 6/12* (2006.01)
*A61B 6/00* (2006.01)
*A61M 25/09* (2006.01)

(52) U.S. Cl.
CPC ........ *A61M 25/0041* (2013.01); *A61M 25/09* (2013.01); *A61M 25/1002* (2013.01); *A61M 29/02* (2013.01); *A61B 2017/246* (2013.01); *A61M 2025/1079* (2013.01); *A61M 2025/1086* (2013.01); *A61M 2210/0618* (2013.01); *A61M 2210/0681* (2013.01)

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,477,438 A | 11/1969 | Allen et al. |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,137 A | 6/1970 | Santomieri |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,802,096 A | 4/1974 | Matern |
| 3,804,081 A | 4/1974 | Kinoshita |
| 3,800,788 A | 7/1974 | White |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,311,146 A | 1/1982 | Wonder |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,441,495 A | 4/1984 | Hicswa |
| 4,445,892 A | 5/1984 | Hussein et al. |
| 4,450,150 A | 5/1984 | Sidman |
| 4,459,977 A | 7/1984 | Pizon et al. |
| 4,464,175 A | 8/1984 | Altman et al. |
| 4,467,790 A | 8/1984 | Schiff |
| 4,471,779 A | 9/1984 | Antoshkiw et al. |
| 4,499,899 A | 2/1985 | Lyons, III |
| 4,517,979 A | 5/1985 | Pecenka |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,592,357 A | 6/1986 | Ersek |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,641,654 A | 2/1987 | Samson et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,682,607 A | 7/1987 | Vaillancourt et al. |
| 4,684,363 A | 8/1987 | Ari et al. |
| 4,686,965 A | 8/1987 | Bonnet et al. |
| 4,691,948 A | 9/1987 | Austin, Jr. et al. |
| 4,696,544 A | 9/1987 | Costella |

(56) References Cited

U.S. PATENT DOCUMENTS

| | | |
|---|---|---|
| 4,700,694 A | 10/1987 | Shishido |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,753,637 A | 6/1988 | Horneffer |
| 4,755,171 A | 7/1988 | Tennant |
| 4,771,776 A | 9/1988 | Powell et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,802,461 A | 2/1989 | Cho |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,834,709 A | 5/1989 | Banning et al. |
| 4,846,186 A | 7/1989 | Box et al. |
| 4,847,258 A | 7/1989 | Sturm et al. |
| 4,851,228 A | 7/1989 | Zenter et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,953,553 A | 9/1990 | Tremulis |
| 4,961,433 A | 10/1990 | Christian |
| 4,966,163 A | 10/1990 | Kraus et al. |
| 4,984,581 A | 1/1991 | Stice |
| 4,986,810 A | 1/1991 | Semrad |
| 4,991,588 A | 2/1991 | Pflueger et al. |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,040,548 A | 8/1991 | Yock |
| 5,041,089 A | 8/1991 | Mueller et al. |
| 5,044,678 A | 9/1991 | Detweiler |
| 5,049,132 A | 9/1991 | Shaffer et al. |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | Lind |
| 5,069,226 A | 12/1991 | Yamauchi et al. |
| 5,084,010 A | 1/1992 | Plaia et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,090,959 A | 2/1992 | Samson et al. |
| 5,099,845 A | 3/1992 | Besz et al. |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,161,534 A | 11/1992 | Berthiaume |
| 5,163,989 A | 11/1992 | Campbell et al. |
| 5,165,420 A | 11/1992 | Strickland |
| 5,167,220 A | 12/1992 | Brown |
| 5,168,864 A | 12/1992 | Skockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,195,971 A | 3/1993 | Sirhan |
| 5,197,457 A | 3/1993 | Adair |
| 5,201,908 A | 4/1993 | Jones |
| 5,207,695 A | 5/1993 | Trout, III |
| 5,211,952 A | 5/1993 | Spicer et al. |
| 5,213,576 A | 5/1993 | Abiuso et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,292,305 A | 3/1994 | Boudewijn et al. |
| 5,295,694 A | 3/1994 | Levin |
| 5,300,085 A | 4/1994 | Yock |
| 5,304,123 A | 4/1994 | Atala et al. |
| 5,306,272 A | 4/1994 | Cohen et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,314,443 A | 5/1994 | Rudnick |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,143 A | 8/1994 | Carroll |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |

(56) References Cited

U.S. PATENT DOCUMENTS

| | | |
|---|---|---|
| 5,368,558 A | 11/1994 | Nita |
| 5,368,566 A | 11/1994 | Crocker |
| 5,370,640 A | 12/1994 | Koloff |
| 5,372,138 A | 12/1994 | Crowley et al. |
| 5,372,584 A | 12/1994 | Zink et al. |
| D355,031 S | 1/1995 | Yoshikawa |
| 5,378,234 A | 1/1995 | Hammerslag et al. |
| 5,385,562 A | 1/1995 | Adams et al. |
| 5,386,817 A | 2/1995 | Jones |
| 5,386,828 A | 2/1995 | Owens et al. |
| 5,391,147 A | 2/1995 | Imran et al. |
| 5,391,179 A | 2/1995 | Mezzoli |
| 5,395,367 A | 3/1995 | Wilk |
| 5,397,305 A | 3/1995 | Kawula et al. |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,309 A | 12/1995 | Sweezer et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,653,690 A | 8/1997 | Booth et al. |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,720,719 A | 2/1998 | Edwards et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,749,357 A | 5/1998 | Linder |
| 5,749,920 A | 5/1998 | Quiachon et al. |
| 5,752,513 A | 5/1998 | Acker et al. |
| 5,752,971 A | 5/1998 | Rosenbluth et al. |
| 5,762,604 A | 6/1998 | Kieturakis |
| 5,766,158 A | 6/1998 | Opolski |
| 5,769,821 A | 6/1998 | Abrahamson et al. |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,823,961 A | 10/1998 | Fields et al. |
| 5,824,044 A | 10/1998 | Quiachon et al. |
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,827,323 A | 10/1998 | Klieman et al. |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,836,951 A | 11/1998 | Rosenbluth et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,882,333 A | 3/1999 | Schaer et al. |
| 5,882,346 A | 3/1999 | Pomeranz et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |

(56) References Cited

U.S. PATENT DOCUMENTS

| | | |
|---|---|---|
| 5,908,407 A | 6/1999 | Frazee et al. |
| 5,916,193 A | 6/1999 | Stevens et al. |
| 5,916,213 A | 6/1999 | Haissaguerre et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,967,984 A | 10/1999 | Chu et al. |
| 5,968,085 A | 10/1999 | Morris et al. |
| 5,971,975 A | 10/1999 | Mills et al. |
| 5,976,074 A | 11/1999 | Moriyama |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,989,025 A | 11/1999 | Conley |
| 5,993,462 A | 11/1999 | Pomeranz et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,022 A | 5/2000 | Ben-Haim |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,102,891 A | 8/2000 | van Erp et al. |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,402 A | 11/2000 | Munoz |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,776 B1 | 1/2001 | Adams et al. |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,238,430 B1 | 5/2001 | Klumb et al. |
| 6,241,519 B1 | 6/2001 | Sedelmayer |
| 6,248,092 B1 | 6/2001 | Miraki et al. |
| 6,249,180 B1 | 6/2001 | Maalej et al. |
| 6,254,550 B1 | 7/2001 | McNamara et al. |
| 6,264,087 B1 | 7/2001 | Whitman |
| 6,268,574 B1 | 7/2001 | Edens |
| 6,270,477 B1 | 8/2001 | Bagaoisan et al. |
| 6,280,433 B1 | 8/2001 | McIvor et al. |
| 6,283,908 B1 | 8/2001 | Aviram et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,304,768 B1 | 10/2001 | Blume et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,328,730 B1 | 12/2001 | Harkrider, Jr. |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,379,319 B1 | 4/2002 | Garibotto et al. |
| 6,381,485 B1 | 4/2002 | Hunter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,436,119 B1 | 8/2002 | Erb et al. |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |

(56) References Cited

U.S. PATENT DOCUMENTS

| | | |
|---|---|---|
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,520,954 B2 | 2/2003 | Ouchi |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,562,022 B2 | 5/2003 | Hoste et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,645,223 B2 | 11/2003 | Boyle et al. |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,833 B2 | 1/2004 | Smith et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,740,191 B2 | 5/2004 | Clarke et al. |
| 6,741,884 B1 | 5/2004 | Freeman et al. |
| 6,743,168 B2 | 6/2004 | Luloh et al. |
| 6,755,812 B2 | 6/2004 | Peterson et al. |
| 6,758,857 B2 | 7/2004 | Cioanta et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,866,669 B2 | 3/2005 | Buzzard et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,953,431 B2 | 10/2005 | Barthel |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,979,979 B2 | 12/2005 | Xu et al. |
| 6,984,203 B2 | 1/2006 | Tartaglia et al. |
| 6,989,024 B2 | 1/2006 | Hebert et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,004,176 B2 | 2/2006 | Lau |
| 7,008,412 B2 | 3/2006 | Maginot |
| 7,011,654 B2 | 3/2006 | Dubrul et al. |
| 7,022,105 B1 | 4/2006 | Edwards |
| 7,037,321 B2 | 5/2006 | Sachdeva |
| 7,043,961 B2 | 5/2006 | Pandey |
| 7,044,964 B2 | 5/2006 | Jang et al. |
| 7,048,711 B2 | 5/2006 | Rosenmann et al. |
| 7,052,474 B2 | 5/2006 | Castell et al. |
| 7,056,284 B2 | 6/2006 | Martone et al. |
| 7,056,287 B2 | 6/2006 | Taylor et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,186,224 B2 | 3/2007 | Windheuser |
| 7,207,981 B2 | 4/2007 | Quinn et al. |

(56) References Cited

U.S. PATENT DOCUMENTS

| | | |
|---|---|---|
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,248,914 B2 | 7/2007 | Hastings et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,309,334 B2 | 12/2007 | von Hoffmann |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,384,407 B2 | 6/2008 | Rodriguez et al. |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,551,758 B2 | 6/2009 | Florent et al. |
| 7,559,925 B2 | 7/2009 | Goldfarb et al. |
| 7,566,300 B2 | 7/2009 | Devierre et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,697,972 B2 | 4/2010 | Verard et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,751,758 B2 | 7/2010 | Yahagi |
| 7,753,929 B2 | 7/2010 | Becker |
| 7,753,930 B2 | 7/2010 | Becker |
| 7,758,497 B2 | 7/2010 | Hern |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| 7,857,750 B2 | 12/2010 | Belafsky |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,927,271 B2 | 4/2011 | Dimitriou et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,075,476 B2 | 12/2011 | Vargas |
| 8,075,478 B2 | 12/2011 | Campos |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,147,545 B2 | 4/2012 | Avior |
| 8,167,821 B2 | 5/2012 | Sharrow |
| 8,172,828 B2 | 5/2012 | Chang et al. |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,414,473 B2 | 4/2013 | Jenkins et al. |
| 8,425,457 B2 | 4/2013 | John et al. |
| 8,439,687 B1 | 5/2013 | Morriss et al. |
| 8,475,360 B2 | 7/2013 | Brown |
| 8,521,259 B2 | 8/2013 | Mandrusov et al. |
| 8,529,439 B2 | 9/2013 | Ito et al. |
| 8,535,707 B2 | 9/2013 | Arensdorf et al. |
| 8,568,439 B2 | 10/2013 | Keith et al. |
| 8,702,626 B1 | 4/2014 | Kim et al. |
| 8,715,169 B2 | 5/2014 | Chang et al. |
| 8,721,591 B2 | 5/2014 | Chang et al. |
| 8,740,292 B2 | 6/2014 | Gopferich et al. |
| 8,740,839 B2 | 6/2014 | Eaton et al. |
| 8,747,389 B2 | 6/2014 | Goldfarb et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,777,926 B2 | 7/2014 | Chang et al. |
| 8,802,131 B2 | 8/2014 | Arensdorf et al. |
| 8,828,041 B2 | 9/2014 | Chang et al. |
| 9,101,574 B2 | 8/2015 | Chang et al. |
| 9,220,879 B2 | 12/2015 | Chang et al. |
| 9,241,834 B2 | 1/2016 | Chang et al. |
| 9,370,649 B2 | 6/2016 | Chang et al. |
| 9,399,121 B2 | 7/2016 | Goldfarb et al. |
| 9,610,428 B2 | 4/2017 | Muni et al. |
| 9,649,477 B2 | 5/2017 | Muni et al. |
| 10,098,652 B2 | 10/2018 | Goldfarb et al. |
| 10,124,154 B2 | 11/2018 | Evard et al. |

(56) References Cited

U.S. PATENT DOCUMENTS

| | | |
|---|---|---|
| 2001/0004644 A1 | 6/2001 | Levin |
| 2001/0005785 A1 | 6/2001 | Sachse |
| 2001/0034530 A1 | 10/2001 | Malackowski et al. |
| 2002/0006961 A1 | 1/2002 | Katz et al. |
| 2002/0013548 A1 | 1/2002 | Hinchliffe |
| 2002/0055746 A1 | 5/2002 | Burke et al. |
| 2002/0068851 A1 | 6/2002 | Gravenstein et al. |
| 2002/0077593 A1 | 6/2002 | Perkins et al. |
| 2002/0090388 A1 | 7/2002 | Humes et al. |
| 2002/0115963 A1 | 8/2002 | Clarke et al. |
| 2002/0161389 A1 | 10/2002 | Boyle et al. |
| 2003/0009095 A1 | 1/2003 | Skarda |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0051733 A1 | 3/2003 | Kotmel et al. |
| 2003/0073900 A1 | 4/2003 | Senarith et al. |
| 2003/0074045 A1 | 4/2003 | Buzzard et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2003/0220551 A1 | 11/2003 | Kimball et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0064150 A1 | 4/2004 | Becker |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0220516 A1 | 11/2004 | Solomon et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0038319 A1 | 2/2005 | Goldwasser et al. |
| 2005/0055077 A1 | 3/2005 | Marco |
| 2005/0059930 A1 | 3/2005 | Garrison et al. |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228224 A1 | 10/2005 | Okada et al. |
| 2005/0234507 A1 | 10/2005 | Geske et al. |
| 2005/0240120 A1 | 10/2005 | Modesitt |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0250105 A1 | 10/2007 | Ressemann et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0132938 A1 | 6/2008 | Chang et al. |
| 2008/0172033 A1 | 7/2008 | Keith et al. |
| 2008/0183128 A1 | 7/2008 | Morriss et al. |
| 2008/0188803 A1 | 8/2008 | Jang |
| 2008/0188870 A1 | 8/2008 | Andre et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0087811 A1 | 4/2010 | Herrin et al. |
| 2010/0114066 A1 | 5/2010 | Makower et al. |
| 2010/0174138 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0211007 A1 | 8/2010 | Lesch, Jr. et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | Chang et al. |
| 2013/0261388 A1 | 10/2013 | Jenkins et al. |
| 2014/0200444 A1 | 7/2014 | Kim et al. |
| 2014/0296898 A1 | 10/2014 | Chang et al. |
| 2014/0330074 A1 | 11/2014 | Morriss et al. |
| 2014/0336575 A1 | 11/2014 | Muni et al. |
| 2014/0336693 A1 | 11/2014 | Goldfarb et al. |
| 2014/0350465 A1 | 11/2014 | Muni et al. |
| 2014/0364725 A1 | 12/2014 | Makower |
| 2015/0088188 A1 | 3/2015 | Muni et al. |
| 2015/0165175 A1 | 6/2015 | Evard et al. |
| 2015/0165176 A1 | 6/2015 | Makower et al. |
| 2015/0182735 A1 | 7/2015 | Chang et al. |
| 2015/0209055 A1 | 7/2015 | Chang et al. |
| 2015/0250992 A1 | 9/2015 | Morriss et al. |
| 2016/0192830 A1 | 7/2016 | Goldfarb et al. |
| 2016/0270863 A1 | 9/2016 | Makower |

(56) References Cited

U.S. PATENT DOCUMENTS

| | | | |
|---|---|---|---|
| 2017/0007281 A1 | 1/2017 | Goldfarb et al. | |
| 2017/0071625 A1 | 3/2017 | Chang et al. | |

FOREIGN PATENT DOCUMENTS

| | | |
|---|---|---|
| CN | 2151720 | 1/1994 |
| CN | 2352818 | 12/1999 |
| CN | 201005758 Y | 1/2008 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1112103 | 7/2001 |
| EP | 1166710 | 1/2002 |
| EP | 1413258 | 4/2004 |
| EP | 1944053 | 7/2008 |
| FR | 2662083 | 11/1991 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | S61-16750 | 1/1986 |
| JP | 10-24098 | 1/1989 |
| JP | H10-034376 | 2/1989 |
| JP | H01-305965 | 12/1989 |
| JP | 3-503011 | 7/1991 |
| JP | 3-504935 | 10/1991 |
| JP | 4-221313 | 8/1992 |
| JP | 4-224766 | 8/1992 |
| JP | H5-503650 | 6/1993 |
| JP | 5-211985 | 8/1993 |
| JP | H05-506805 | 10/1993 |
| JP | H06-017751 | 3/1994 |
| JP | 6-277296 | 10/1994 |
| JP | 7-327916 | 12/1995 |
| JP | 8-317989 | 12/1996 |
| JP | H10-501159 | 2/1998 |
| JP | H10-094543 | 4/1998 |
| JP | 11-507251 | 6/1999 |
| JP | 2000-501634 | 2/2000 |
| JP | 2000-126303 | 5/2000 |
| JP | 2001-025508 | 1/2001 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 2004-357728 | 12/2004 |
| JP | 2005-323702 | 11/2005 |
| JP | 2005-532869 | 11/2005 |
| JP | 2008-539031 | 11/2008 |
| RU | 2108764 | 4/1998 |
| RU | 2213530 | 10/2003 |
| SU | 1662571 | 7/1994 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 94/021320 | 9/1994 |
| WO | WO 95/002430 | 1/1995 |
| WO | WO 96/029071 | 9/1996 |
| WO | WO 97/021461 | 6/1997 |
| WO | WO 98/055174 | 12/1998 |
| WO | WO 99/000064 | 1/1999 |
| WO | WO 99/024106 | 5/1999 |
| WO | WO 99/026692 | 6/1999 |
| WO | WO 99/030655 | 6/1999 |
| WO | WO 99/032041 | 7/1999 |
| WO | WO 99/059649 | 11/1999 |
| WO | WO 00/009190 | 2/2000 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 00/067834 | 11/2000 |
| WO | WO 01/005462 | 1/2001 |
| WO | WO 01/045572 | 6/2001 |
| WO | WO 01/054558 | 8/2001 |
| WO | WO 01/056481 | 8/2001 |
| WO | WO 01/068178 | 9/2001 |
| WO | WO 01/070325 | 9/2001 |
| WO | WO 01/074266 | 10/2001 |
| WO | WO 01/082800 | 11/2001 |
| WO | WO 01/097895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/045387 | 6/2004 |
| WO | WO 04/058045 | 7/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/034203 | 3/2007 |
| WO | WO 07/035204 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

AUST, R., et al. 'The Functional Size of the Human Maxillary Ostium in Vivo' Acta. Otolaryn (9178) vol. 78 pp. 432-435.

Baim, D.S., MD 'Grossman's Cardiac Catheterization, Angiography, and Intervention' (2000) Lippincott Williams & Wilkins pp. 76, 84 & 214.

Barrett, S. 'Be Wary of Neurocranial Restructuring (NCR)' Chirobase; Jul. 2003; www.chirobase.org/06DD/ncr.html.

(56) References Cited

OTHER PUBLICATIONS

Bartal, N. 'An Improved stent for Use in the Surgical Management of Congenital Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. www.inventors.about.com/library/inventors/blcatheter.htm?p=1.
Benninger et al.; Adult Chronic Rhinosinusitis: Definitions, Diagnosis, Epidemiology, and Pathophysiology Arch Otolaryngology Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115. No. 4 pp. 293-299.
Casiano et al. 'Endoscopic Lothrop Procedure: The University of Miami Experience' Amencan Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Deliver' Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers-General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngology Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.

Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Applications' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Frontal Sinsus' OASIS-Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Surgery and Hand Surgery (1999) vol. 33 pp. 321-324.
Hojo, M. et al, 'Electrophilic Substitutions of Olefinic Hydrogens II. Acylation of Vinyl Ethers and N Vinyl Amindes Chemistry Letters' (1976) pp. 499-502. Chemical Society of Japan.
Hopf, J.U.G. et al. 'Miniature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Qperationa.Medicine/DATA. 2001 pp. 1-6.

(56) References Cited

OTHER PUBLICATIONS

Hybels, R.L. 'Transillumination During Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copynght 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinolugy. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium (1993) Jul. 21-24.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com-MicroFrance Catalog Browser. www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.

Min, Y-G et al. 'Mucociliary Activity and Histopathology of Sinus Mucosa in Experimental Maxillary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Park, K. et al. 'Biodegradable Hydrogels for Drug Delivery' (1993) Technomic Publishing Inc. Lancaster.
Piccirillo, J.F. et al. 'Psychometric and Clinometric Validity of the 20-Item Sino-Nasal Outcome test (SNOT-20)' Copyright 1996 Washington University, St. Louis, MO.
Piers, et al. 'A Flexible distal Tip with Two Degrees of Freedom for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluoroscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1. pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. 1 (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.

(56) References Cited

OTHER PUBLICATIONS

Strohm, et al. Die Behandlung von Stenosen der oberen Luftwege mittels rontgenologisch gesteuerter Ballondilation (Sep. 25, 1999) pp. 1-4.
Strohm, et al 'Le Traitement Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxilla Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steroid Distribution' Rhinology. vol. 37 (1999) pp. 69-73.
Weiner, R.I., D.O., et al., 'Development and Application of Trans Septal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80, pp. 10-12.
Zimarino, M., M.D., et al., 'Initial Experience with the EuropassTM: A new Ultra-Low-Profile Monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.
Australian Office Action dated Feb. 12, 2014 for Application No. AU 2012202103.
Australian Office Action dated Aug. 1, 2014 for Application No. AU 2012244072.
Australian Office Action dated Sep. 17, 2014 for Application No. AU 2012202103.
Australian Office Action dated Sep. 30, 2014 for Application No. AU 2009293312.
Australian Office Action dated Oct. 1, 2014 for Application No. AU 2009333010.
Australian Office Action dated Jul. 8, 2015 for Application No. AU 2012244072.
Canadian Office Action dated Jul. 10, 2015 for Application No. CA 2,617,054.
Canadian Office Action dated Dec. 16, 2015 for Application No. CA 2,751,665.
Chinese Office Action, First Office Action dated Jan. 29, 2013 for CN 200980152995.1.
Chinese Office Action, First Office Action dated Nov. 5, 2012 for CN 200980137396.1.
Chinese Office Action, Decision of Rejection, dated 2014 for Application No. CN 200980152995.1.
Chinese Office Action, Third Office Action, dated Feb. 27, 2014 for Application No. CN 200980152995.1.
Chinese Office Action and Search Report dated Feb. 10, 2015 for Application No. CN 201310672731.6.
Chinese Search Report dated Jan. 11, 2013 for Application No. CN 200980152995.0.
Chinese Search Report dated Oct. 29, 2012 for Application No. CN 200980137396.1.
European Communication dated Jan. 7, 2013 for Application No. EP 08746715.5.
European Communication dated Apr. 11, 2013 for Application No. EP 05778834.1.
European Communication dated Apr. 19, 2012 for Application No. EP 08746715.5.
European Communication dated May 10, 2013 for Application No. EP 06751637.7.
European Communication dated Jun. 19, 2009 for Application No. EP 05773189.
European Communication dated Aug. 1, 2012 for Application No. EP 06784759.0.
European Communication dated Aug. 24, 2012 for Application No. EP 05798331.4.
European Communication dated Sep. 4, 2008 for Application No. EP 05773189.
European Communication dated Nov. 9, 2012 for Application No. EP 07750248.2.
European Communication dated Sep. 27, 2011 for Application No. EP 06800540.4.
European Communication dated Sep. 3, 2013 for Application No. EP 12182998.0.
European Communication dated Feb. 26, 2014 for Application No. EP 06800540.4.
European Communication dated Aug. 11, 2014 for Application No. EP 12182998.0.
European Communication dated Aug. 26, 2014 for Application No. EP 12183000.4.
European Communication dated Nov. 26, 2014 for Application No. EP 07836108.6.
European Communication dated Feb. 17, 2016 for Application No. EP 12162712.9.
European Exam Report dated Feb. 8, 2007 for Application No. EP 02716734.5.
European Exam Report dated Feb. 22, 2006 for Application No. EP 02716734.5.
European Search Report and Written Opinion dated Sep. 11, 2009 for Application No. EP 06815174.
European Search Report dated Jan. 9, 2013 for Application No. EP 12183000.
European Search Report dated Jan. 11, 2013 for Application No. EP 12183002.
European Search Report dated Mar. 16, 2010 re Application No. EP 06718986.
European Search Report dated Jul. 23, 2012 for Application No. EP 12162709.
European Search Report dated Jul. 24, 2012 for Application No. EP 12162712.
European Search Report dated Aug. 6, 2013 for Application No. EP 13172140.
European Search Report dated Aug. 31, 2012 for Application No. EP 12173295.
European Search Report dated Sep. 9, 2013 for Application No. EP 13179223.

(56) References Cited

OTHER PUBLICATIONS

European Search Report dated Sep. 27, 2011 for Application No. EP 10182961.
European Search Report dated Sep. 29, 2011 for Application No. EP 10182893.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated May 19, 2015 for Application No. EP 08746464.0.
European Search Report dated Jun. 23, 2015 for Application No. EP 12162712.9.
European Search Report dated Jun. 23, 2015 for Application No. EP 12162709.5.
Extended European Search Report dated Jan. 27, 2014 for Application No. EP 108426321.1.
Extended European Search Report dated Sep. 15, 2015 for Application No. EP 15163549.7.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Sep. 25, 2007 for Application No. PCT/US06/002004.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability and Written Opinion dated Nov. 18, 2008 for Application No. PCT/US07/11449.
International Preliminary Report on Patentability dated Feb. 15, 2008 for Application No. PCT/US05/13617.
International Preliminary Report on Patentability dated Jun. 29, 2011 for Application No. PCT/US2009/069143.
International Preliminary Report on Patentability dated Aug. 7, 2006 for Application No. PCT/US05/25371.
International Search Report and Written Opinion dated Apr. 10, 2006 for Application No. PCT/US05/25371.
International Search Report and Written Opinion dated Jul. 21, 2008 for Application No. PCT/US05/033090.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report and Written Opinion dated Oct. 6, 2010 for Application No. PCT/US2010/040548.
International Written Opinion dated Aug. 9, 2011 for Application No. PCT/US2011/038751.
International Search Report dated Mar. 31, 2010 for Application No. PCT/US2009/069143.
International Search Report dated May 8, 2007 for Application No. PCT/US2006/16026.
International Search Report dated May 18, 2012 for Application No. PCT/US2011/052321.
International Search Report dated May 29, 2008 for Application No. PCT/US07/021170.
International Search Report dated May 29, 2008 for Application No. PCT/US07/021922.
International Search Report dated Jun. 3, 2002 for Application No. PCT/EP02/01228.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 8, 2010 for Application No. PCT/US2010/027837.
International Search Report dated Jul. 17, 2008 for Application No. PCT/US06/036960.
International Search Report dated Aug. 17, 2007 for Application No. PCT/US05/013617.
International Search Report dated Aug. 25, 2008 for Application No. PCT/US2008/000911.
International Search Report dated Aug. 29, 2007 for Application No. PCT/US06/002004.
International Search Report dated Aug. 9, 2011 for Application No. PCT/US2011/038751.
International Search Report dated Sep. 10, 2008 for Application No. PCT/US07/016212.
International Search Report dated Sep. 25, 2007 for Application No. PCT/US06/037167.
International Search Report dated Oct. 15, 2008 for Application No. PCT/US2008/061048.
International Search Report dated Oct. 19, 2007 for Application No. PCT/US07/003394.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
Japanese Office Action, Examiner's Decision of Refusal dated Oct. 18, 2011 for Application. No. JP 2007-509632.
Japanese Office Action, Notification of Reasons for Refusal dated Jan. 24, 2012 for Application No. JP 2007-532485.
Japanese Office Action, Notification of Reasons for Refusal dated Apr. 26, 2011 for Application No. JP 2007-532485.
Japanese Office Action, Notification of Reasons for Refusal dated Jun. 25, 2013 for Application No. JP 2012-131840.
Japanese Office Action, Notification of Reasons for Refusal dated Aug. 16, 2011 for Application No. JP 2008-516013.
Japanese Office Action, Notification of Reasons for Refusal dated Sep. 18, 2013 for Application No. JP 2011-527942.
Japanese Office Action, Notification of Reasons for Refusal dated Nov. 8, 2011 for Application No. JP 2008-524250.
Japanese Office Action, Notification of Reasons for Refusal dated Nov. 12, 2013 for Application No. JP 2011-542562.
Japanese Office Action, Notification of Reasons for Refusal dated Jan. 7, 2014 for Application No. JP 2012-266049.
Japanese Office Action, Reasons for Refusal, dated Sep. 2, 2014 for Application No. JP 2012-544859.
Japanese Office Action, Reasons for Refusal, dated Jun. 9, 2015 for Application No. JP 2014-147174.
Japanese Office Action, Notification of Reasons for Refusal dated 03/2x92/2016 for Application No. JP 2012-266049.
Partial European Search Report dated Mar. 25, 2008 for Application No. EP 07252018.
Partial European Search Report dated Sep. 20, 2007 for Application No. EP 07252018.
Partial International Search Report dated Feb. 7, 2012 for Application No. PCT/US2011/052321.
PCT Search Report dated Nov. 30, 2009 for Application No. UPCT/US2009/057203.
Russian Office Action dated Mar. 19, 2013 for Application No. RU 2011130530.

(56) References Cited

OTHER PUBLICATIONS

Russian Office Action dated Sep. 28, 2012 for Application No. RU 2011130530.
Supplemental European Search Report dated Jan. 28, 2011 for Application No. EP 07777004.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Mar. 31, 2011 for Application No. EP 05798331.
Supplemental European Search Report dated Jun. 22, 2010 for Application No. EP 06784759.
Supplemental European Search Report dated Aug. 30, 2011 for Application No. EP 06800540.
Supplemental European Search Report dated Sep. 23, 2010 for Application No. EP 08746715.
Supplemental European Search Report dated Sep. 29, 2011 for Application No. EP 07750248.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Rqport dated Jan. 14, 2014 for Application No. EP 13184009.
Supplemental European Search Report dated Jan. 17, 2014 for Application No. EP 1084263.
Supplemental European Search Report dated Feb. 13, 2014 for Application No. EP 08746464.
Supplemental European Search Report dated Dec. 9, 2014 for Application No. EP 07839152.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 14/221,550, filed Mar. 21, 2014.
U.S. Appl. No. 11/789,705, filed Apr. 24, 2007.
U.S. Appl. No. 11/804,308, filed May 16, 2007.
U.S. Appl. No. 11/804,309, filed May 16, 2007.
U.S. Appl. No. 14/221,621, filed Mar. 21, 2014.
U.S. Appl. No. 14/221,714, filed Mar. 21, 2014.
U.S. Appl. No. 14/265,888, filed Apr. 30, 2014.
U.S. Appl. No. 14/266,002, filed Apr. 30, 2014.
U.S. Appl. No. 14/266,025, filed Apr. 30, 2014.
U.S. Appl. No. 14/327,593, filed Jul. 10, 2014.
U.S. Appl. No. 14/464,948, filed Aug. 21, 2014.
U.S. Appl. No. 14/993,444, filed Jan. 12, 2016.
U.S. Appl. No. 15/083,826, filed Mar. 29, 2016.
U.S. Appl. No. 15/417,655.
U.S. Appl. No. 15/417,712.
U.S. Appl. No. 15/443,319.
U.S. Appl. No. 15/465,978.
U.S. Appl. No. 15/595,319.
U.S. Appl. No. 15/624,093.
U.S. Appl. No. 15/624,111.
U.S. Appl. No. 15/651,101.
U.S. Appl. No. 15/795,834.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.

(56) References Cited

OTHER PUBLICATIONS

U.S. Appl. No. 61/084,949, filed Jul. 30, 2008.
U.S. Appl. No. 10/829,917.
U.S. Appl. No. 10/912,557.
U.S. Appl. No. 10/944,270.
U.S. Appl. No. 11/150,847.
U.S. Appl. No. 11/193,020.
U.S. Appl. No. 11/355,512.
U.S. Appl. No. 11/436,892.
U.S. Appl. No. 11/647,530.
U.S. Appl. No. 11/789,704.
U.S. Appl. No. 11/789,705.
U.S. Appl. No. 11/803,695.
U.S. Appl. No. 11/804,308.
U.S. Appl. No. 11/929,667.
U.S. Appl. No. 11/929,808.
U.S. Appl. No. 12/143,698.
U.S. Appl. No. 12/184,166.
U.S. Appl. No. 12/496,226.
U.S. Appl. No. 12/639,919.
U.S. Appl. No. 12/649,027.
U.S. Appl. No. 12/793,352.
U.S. Appl. No. 12/949,708.
U.S. Appl. No. 13/301,406.
U.S. Appl. No. 13/451,453.
U.S. Appl. No. 13/858,580.
U.S. Appl. No. 13/867,972.
U.S. Appl. No. 14/221,550.
U.S. Appl. No. 14/221,714.
U.S. Appl. No. 14/265,787.
U.S. Appl. No. 14/265,888.
U.S. Appl. No. 14/266,002.
U.S. Appl. No. 14/327,593.
U.S. Appl. No. 14/464,948.
U.S. Appl. No. 14/515,687.
U.S. Appl. No. 14/566,845.
U.S. Appl. No. 14/567,051.
U.S. Appl. No. 14/614,799.
U.S. Appl. No. 14/658,432.
U.S. Appl. No. 14/993,444.
U.S. Appl. No. 15/083,826.
U.S. Appl. No. 15/187,938.
Eurppean Communication dated Sep. 26, 2016 for Application No. EP 12162712.9.
European Search Report dated Jan. 27, 2014 for Application No. EP 13184009.2.
European Search Report dated Jun. 28, 2017 for Application No. EP 17159646.3.
"Durometer Made Easy Durometer Hardness Scales—General Reference Guide." Paramount Industries, Inc. 2008. Accessed online: http://www.paramountind.com/pdfs/paramount_durometer_scale_guide.pdf
"DurometerShoreHardnessScale." Smooth-On, Inc. 2016. Accessed online: https://www.smooth-on.com/page/durometer-shore-hardness-scale/.
Merriam-Webster definition of "lumen" as accessed Jun. 10, 2016, http://www.merriam-webster.com/dictionary/lumen.
Nasal Surgery and Accessories, Jan. 25, 2007; www.technologyforlife.com.au/ent/nasal.html.
Canadian Office Action dated Jun. 20, 2016 for Application No. CA 2,617,054.
European Communication dated Sep. 26, 2016 for Application No. EP 12162712.9.
European Communication dated May 12, 2012 for Application No. EP 09792627.3.
European Communication dated Jul. 14, 2017 for Application No. EP 06784759.0.
European Communication dated Aug. 2, 2017 for Application No. EP 12173295.2.
European Seach Report dated Jan. 27, 2014 for Application No. EP 13184009.2.
European Search Report dated Jan. 28, 2017 for Application No. EP 17159646.3.
Supplemental European Search Report dated Mar. 24, 2010 for Application No. EP 07836108.6.
Supplemental European Search Report dated Sep. 8, 2011 for Application No. EP 06800540.4.
Supplemental European Search Report dated Feb. 27, 2014 for Application No. EP 08746464.0.
Supplemental European Search Report dated Dec. 17, 2014 for Application No. EP 07839152.1.

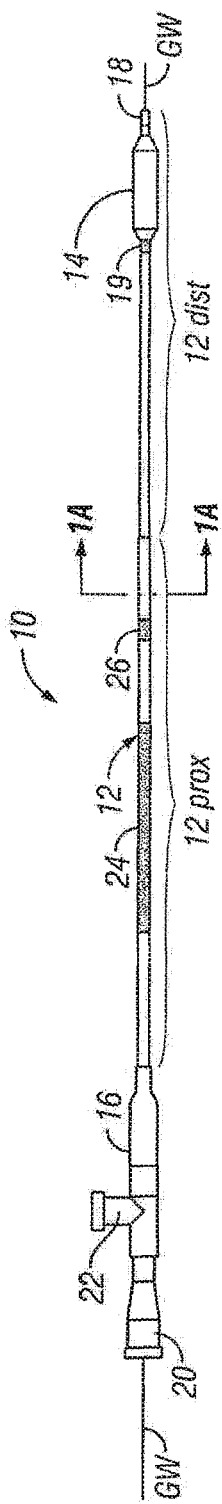
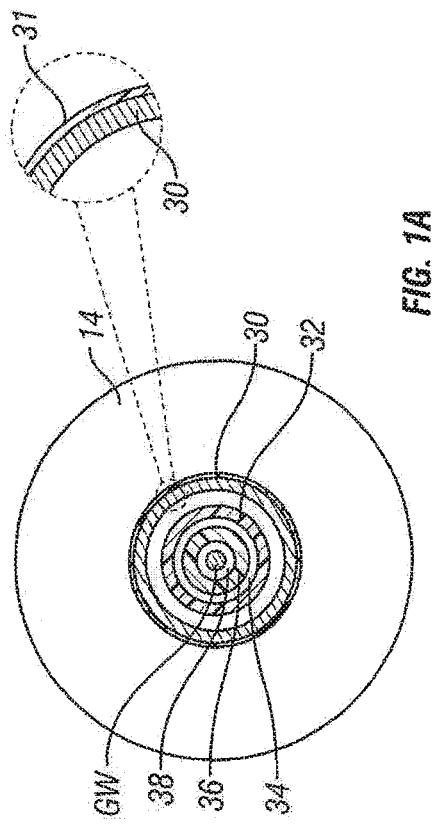
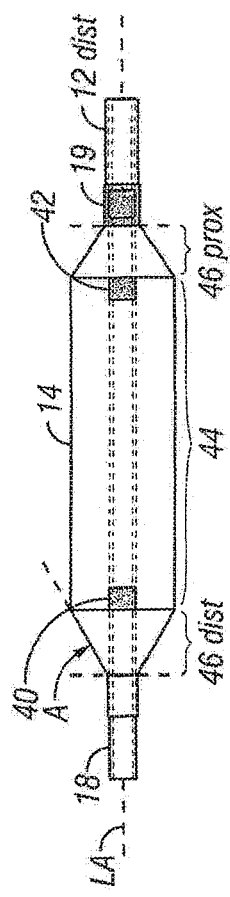
FIG. 1
FIG. 1A
FIG. 1B

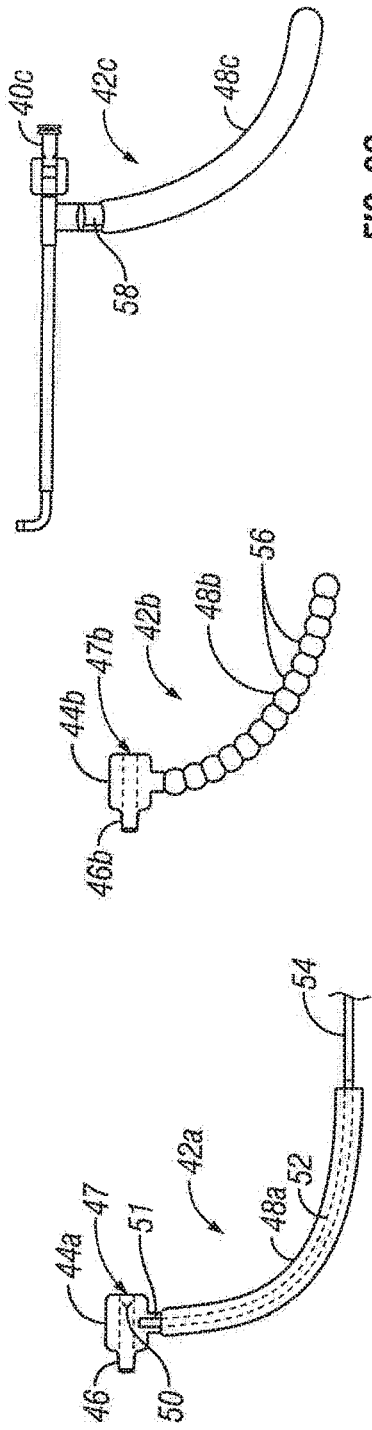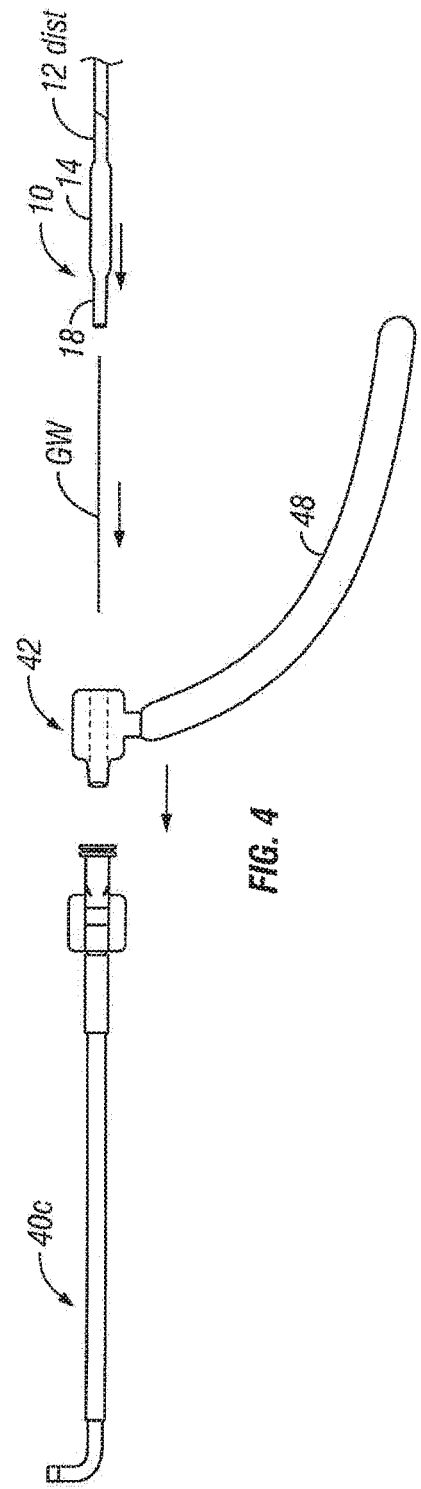

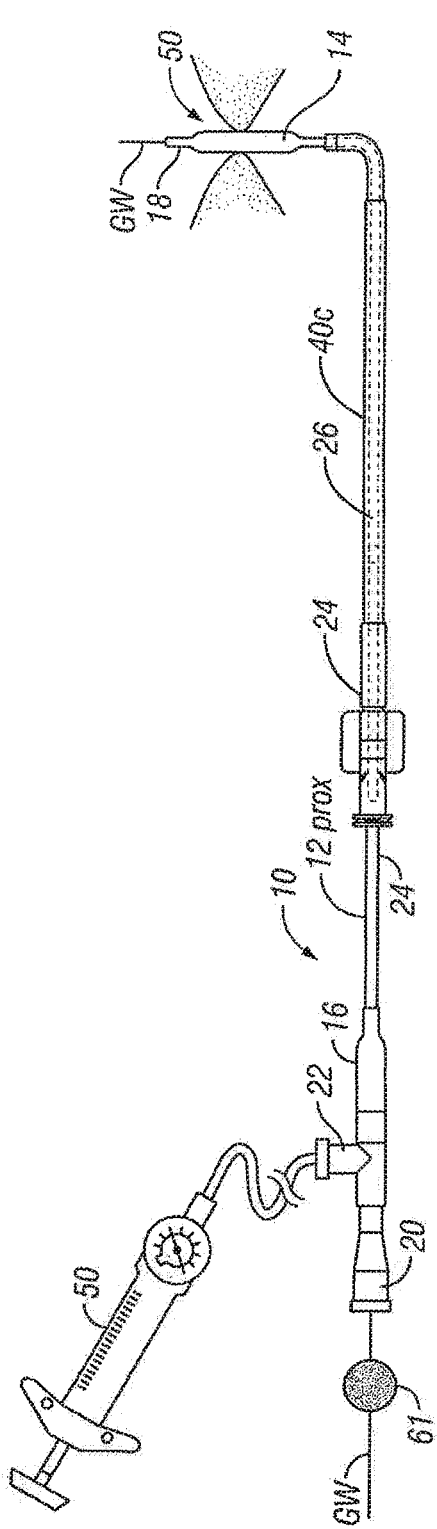
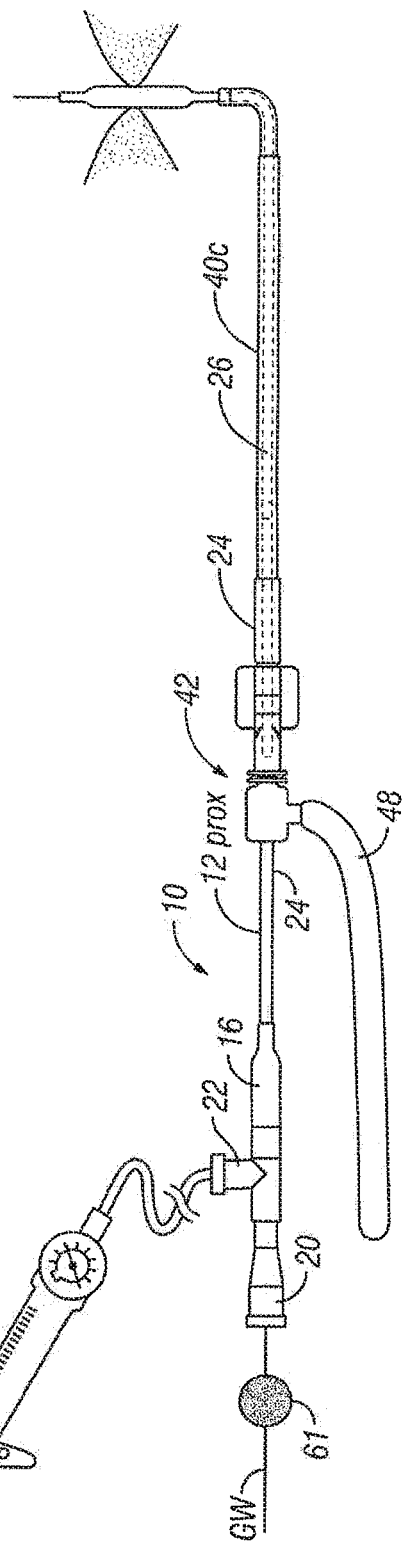
FIG. 5
FIG. 6

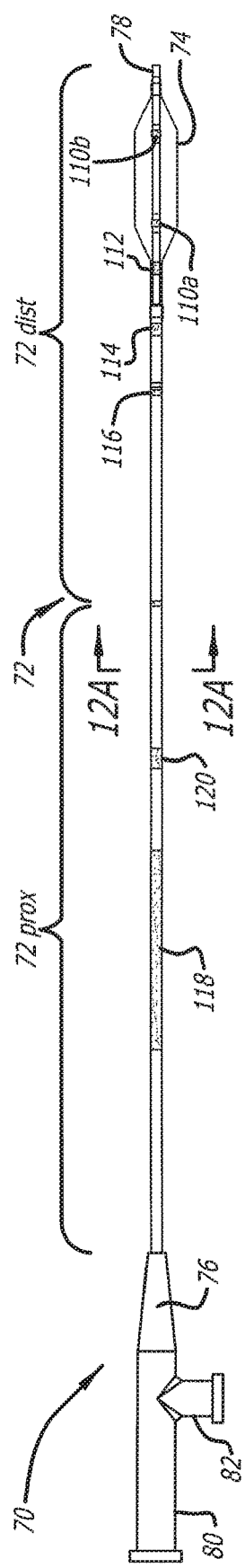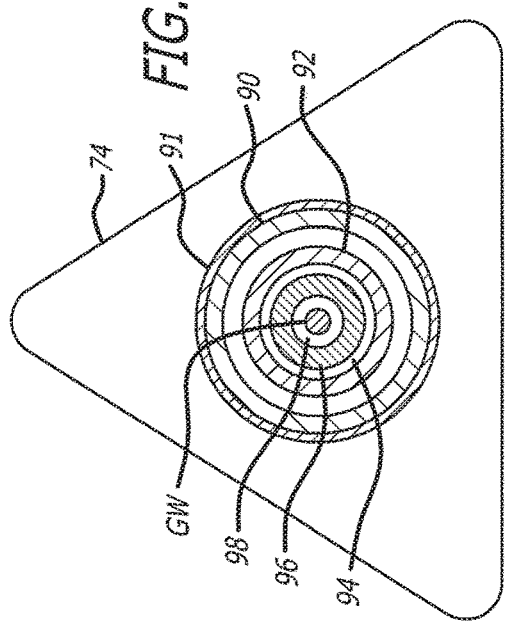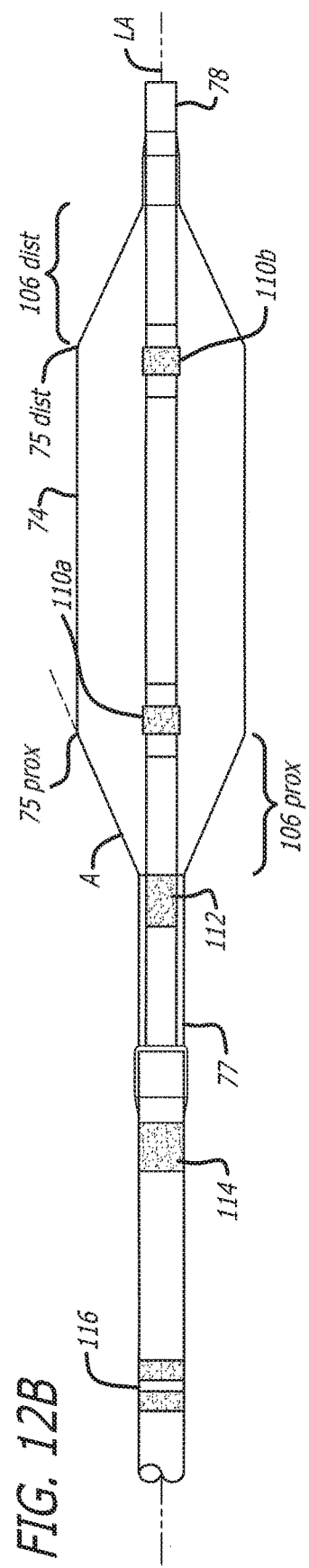

SYSTEMS AND METHODS FOR TRANSNASAL DILATION OF PASSAGEWAYS IN THE EAR, NOSE OR THROAT

RELATED APPLICATIONS

This application is a continuation of U.S. patent application Ser. No. 15/187,938, entitled "Systems and Methods for Transnasal Dilation of Passageways in the Ear, Nose or Throat," filed Jun. 21, 2016, issued as U.S. Pat. No. 10,098,652 on Oct. 16, 2018, which is a division of U.S. patent application Ser. No. 12/496,226, entitled "Systems and Methods for Transnasal Dilation of Passageways in the Ear, Nose or Throat," filed Jul. 1, 2009, issued as U.S. Pat. No. 9,399,121 on Jul. 26, 2016, which is a continuation in part of U.S. patent application Ser. No. 11/789,704 entitled "Systems and Methods for Transnasal Dilation of Passageways in the Ear, Nose and Throat," filed Apr. 24, 2007, issued as U.S. Pat. No. 8,747,389 on Jun. 10, 2014, which is a continuation in part of U.S. patent application Ser. No. 11/355,512 entitled "Devices, Systems and Methods Useable for Treating Frontal Sinusitis," filed Feb. 16, 2006, issued as U.S. Pat. No. 8,894,614 on Nov. 25, 2014, which is a is a continuation in part of U.S. patent application Ser. No. 11/150,847 entitled "Devices, Systems and Methods Useable for Treating Sinusitus," filed on Jun. 10, 2005, issued as U.S. Pat. No. 7,803,150 on Sep. 28, 2010, which is a continuation in part of U.S. patent application Ser. No. 10/944,270 entitled "Apparatus and Methods for Dilating and Modifying Ostia of Paranasal Sinuses and Other Intranasal or Paranasal Structures," filed on Sep. 17, 2004, which published as U.S. Publication No. 2006/0004323 on Jan. 5, 2006, now abandoned, which is a continuation in part of U.S. patent application Ser. No. 10/829,917 entitled "Devices, Systems and Methods for Diagnosing and Treating Sinusitis and Other Disorders of the Ears, Nose and/or Throat," filed on Apr. 21, 2004, issued as U.S. Pat. No. 7,654,997 on Feb. 2, 2010, the entire disclosures of each such application being expressly incorporated herein by reference.

FIELD OF INVENTION

The present invention relates generally to medical devices and methods and particularly to balloon catheters and other devices that may be inserted through the nose and used to dilate the ostia of paranasal sinuses for treatment of sinusitis.

BACKGROUND

The paranasal sinuses are hollow cavities in the skull connected by small openings, known as ostia, to the nasal canal. Normally, air passes into and out of the paranasal sinuses through the ostia. Also, mucus is continually formed by the mucosal lining of the sinus and drains through the ostia and into the nasal canal.

Sinusitis is a general term that refers to inflammation in one or more of the paranasal sinuses. Acute sinusitis can be associated with upper respiratory infections or allergic conditions which cause tissue swelling and temporarily impedes normal trans-ostial drainage and ventilation of the sinuses, thereby resulting in some collection of mucous and possibly infection within the sinus cavities. Chronic sinusitis is a long term condition characterized by persistent or long term narrowing or blockage of the sinus ostia, resulting in chronic infection and inflammation of the sinuses. Chronic sinusitis is often associated with long standing respiratory allergies, nasal polyps, hypertrophic nasal turbinates and/or deviated internasal septum. While acute sinusitis is typically caused by infection with a single pathogen (e.g., one type of bacteria, one type of virus, one type of fungus, etc.), chronic sinusitis is often associated with multiple pathogen infections (e.g., more than one type of bacteria or more than one genus of microorganism).

Chronic sinusitis, if left untreated, can result in irreparable damage to the tissues and/or bony structures of the paranasal anatomy. The initial treatment of chronic sinusitis usually involves the use of drugs such as decongestants, steroid nasal sprays and antibiotics (if the infection is bacterial). In cases where drug treatment alone fails to provide permanent relief, surgical intervention may be indicated.

Functional endoscopic sinus surgery (FESS) is commonly performed use an endoscope and various rigid instruments inserted through the patient's nostril. The endoscope is used to visualize the positioning and use of the operative instruments to perform tasks intended to improve sinus drainage, such as removal of polyps, straightening of deviated septum and excision of mucous membrane and bone to enlarge the narrow the sinus ostia or to create new openings into the sinuses.

Recently the technique known as the Balloon Sinuplasty™ procedure has been developed by Acclarent, Inc. of Menlo Park, Calif. for treatment of sinusitis. A number of copending United States patent applications, including patent application Ser. No. 11/789,704, issued as U.S. Pat. No. 8,747,389 on Jun. 10, 2014, Ser. No. 11/355,512, issued as U.S. Pat. No. 8,894,614 on Nov. 25, 2014, Ser. No. 11/150,847, issued as U.S. Pat. No. 7,803,150 on Sep. 28, 2010, Ser. No. 10/944,270, published as U.S. Publication No. 2006/0004323 on Jan. 5, 2006, and Ser. No. 10/829,917, issued as U.S. Pat. No. 7,654,997 on Feb. 2, 2010, describe various embodiments of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into affected paranasal sinus. Thereafter, a dilation catheter having an expandable dilator (e.g., an inflatable balloon) is advanced over the guidewire to a position where the dilator is positioned within the ostium of the affected paranasal sinus. The dilator is then expanded causing dilation of the ostium and remodeling of bone adjacent to the ostium, without required incision of the mucosa or removal of any bone. The catheters and guidewire are then removed and the dilated ostium allows for improved drainage from and ventilation of the affected paranasal sinus.

U.S. patent application Ser. No. 11/789,704, issued as U.S. Pat. No. 8,747,389 on Jun. 10, 2014, Ser. No. 11/355,512, issued as U.S. Pat. No. 8,894,614 on Nov. 25, 2014, Ser. No. 11/150,847, issued as U.S. Pat. No. 7,803,150 on Sep. 28, 2010, Ser. No. 10/944,270, published as U.S. Publication No. 2006/0004323 on Jan. 5, 2006, and Ser. No. 10/829,917, issued as U.S. Pat. No. 7,654,997 on Feb. 2, 2010, also describe methods for transnasal dilation of other passageways in the ear, nose and/or throat, such as the Eustachian tube and nasolacrimal duct.

SUMMARY

In one embodiment, there is provided a dilation catheter device and system that is useable for dilating the ostium of a paranasal sinus, or other passageway within the ear, nose or throat. This dilation catheter device and system is constructed in a manner that facilitates ease of use by the operator and, in at least some cases, allows the dilation procedure to be performed by a single operator, thereby minimizing the number of personnel required for the procedure. Additionally, the dilation catheter device and system of the present invention is useable in conjunction with an endoscope and/or a fluoroscope to provide for easy manipulation and positioning of the devices and real time visualization of the entire procedure or selected portions thereof. In some embodiments, an optional handle may be attached to the dilation catheter or to a guide catheter through which the dilation catheter is inserted and such handle may be graspable along with another device (e.g., an endoscope) by a single hand. In this manner, the operator may control the dilation catheter and another device (e.g., an endoscope) with one hand while being free to use his other hand for other purposes.

Further in one embodiment, there are provided systems for treating a disease or disorder of the ear, nose or throat of a human or animal subject. Such systems generally comprise a guide catheter and a working catheter. The working catheter is advanceable through the guide catheter. The guide catheter has a substantially rigid shaft and the working catheter has a proximal portion that is substantially rigid. The working catheter also has a distal portion that is more flexible than the substantially rigid proximal portion. The working catheter is sized relative to the guide catheter so that, at least when the distal portion of the working catheter is advanced out of a distal opening of the guide catheter and the working element is being used to perform a desired diagnostic or therapeutic task, only the substantially rigid proximal portion (or some portion thereof) will extend out of the proximal opening of the guide catheter. In some embodiments, the working catheter may additionally be sized relative to the guide catheter so that the working catheter is initially advanceable to a first position where its distal end of the working catheter has not yet emerged out of the distal end of the guide catheter but only the substantially rigid proximal portion of the working catheter is protruding out of the proximal end of the guide catheter.

Still further in accordance with another embodiment, there are provided sinus ostium dilation catheter devices that generally comprise an elongate catheter shaft having proximal shaft section that is substantially rigid and a distal shaft section that is more flexible than the proximal shaft section. In some embodiments, the proximal shaft section may extend along at least about 50% of the overall length of the device. A guidewire lumen extends through at least a portion of the catheter shaft to facilitate advancement of the catheter over a guidewire. A dilator is located on the distal shaft section, such dilator having a non-expanded configuration and an expanded configuration.

Still further in accordance with one embodiment, there are provided methods for dilating the ostia of paranasal sinuses and other passageways within the ear, nose or throat of a human or animal subject. In general, such methods comprise the steps of a) inserting a guide catheter having a proximal end and a distal end through one of the subject's nostrils and positioning the guide catheter within or near the passageway to be dilated, b) inserting, through the guide catheter, a dilation catheter comprising i) an elongate catheter shaft having a proximal end, a distal end, a proximal shaft section that is substantially rigid and a distal shaft section that is more flexible than the proximal shaft section, ii) a guidewire lumen extending through at least a portion of the catheter shaft to facilitate advancement of the catheter over a that is substantially rigid and a distal shaft section that is more flexible than the proximal shaft section, ii) a guidewire lumen extending through at least a portion of the catheter shaft to facilitate advancement of the catheter over a guidewire and iii) a dilator located on the distal shaft section, said dilator being in a non-expanded configuration, c) positioning the dilator within the passageway and d) causing the dilator to expand to an expanded configuration, thereby dilating the passageway.

In still a further embodiment, a balloon dilation catheter device is provided that is useable for dilating an opening in a paranasal sinus. The dilation catheter device includes a catheter shaft having a longitudinal axis, an inflation lumen, a distal end, a proximal end, a proximal shaft section that is substantially rigid and a distal shaft section that is more flexible than the proximal shaft section. Also, the catheter shaft is dark in color. An inflatable balloon is disposed on the distal shaft section. The inflatable balloon is connected to the inflation lumen and the inflatable balloon has a non-circular cross-sectional shape when partially inflated. In this embodiment, the balloon dilation catheter includes a first proximal shaft marker disposed on the proximal shaft section, and the first shaft marker having a significantly lighter color than the catheter shaft. The first proximal shaft marker allows a user to approximate, using direct visualization of the first proximal shaft marker, a position of the balloon relative to a guide catheter through which the balloon catheter is advanced. There is also a first distal shaft marker disposed on the distal shaft section proximal to a proximal end of the balloon and the first distal shaft marker has a significantly lighter color than the catheter shaft. The first distal shaft marker enables a user to approximate, using endoscopic visualization of the first distal shaft marker, a position of the balloon relative to an opening of a paranasal sinus.

In one embodiment, a second proximal shaft marker is disposed on the proximal shaft section distally from the first proximal shaft marker and having a significantly lighter color than the catheter shaft. The first proximal shaft marker has a greater length than the second proximal shaft marker. Further, the length of the first proximal shaft marker is equal to the length from a proximal end of the inflatable balloon to the distal end of the catheter shaft. The first proximal shaft marker is spaced from the distal end of the catheter shaft such that it allows the user to approximate when the distal end of the catheter shaft is located at a distal end of the guide catheter and when the proximal end of the balloon exits a guide catheter, and wherein the second proximal shaft marker allows the user to approximate when the distal end of the catheter shaft is located just proximal to a curve in the guide catheter The balloon dilation catheter device may also include a second distal shaft marker disposed on the distal shaft section proximal to the first distal shaft marker and having a significantly lighter color than the catheter shaft. The first distal shaft marker is disposed at a known distance proximally from the proximal end of the balloon, and the second distal shaft marker is disposed at a known distance proximally from the first distal shaft marker. Also, the first and second distal shaft markers have different appearances. In one embodiment, the first distal shaft marker is disposed approximately one centimeter from the proximal end of the balloon and the second distal shaft marker is disposed approximately two centimeters from the proximal end of the balloon. A third distal shaft marker also may be disposed on the distal shaft section at the proximal end of the balloon.

The balloon dilation catheter device may also include a first radiopaque marker disposed on the distal shaft section and within the inflatable balloon. There may be a second radiopaque marker disposed on the distal shaft section distally from the first radiopaque marker within the balloon. The first and second radiopaque markers are disposed a distance apart from one another to indicate the effective length of the inflatable dilator.

Also, in one embodiment, the inflatable balloon of the balloon dilator catheter device has an approximately triangular cross-section in a partially inflated state. The balloon may also have a balloon neck extending from the balloon proximally along the catheter shaft. The balloon neck allows an endoscopic marker to be disposed on the distal shaft section and underneath the balloon neck.

In an embodiment of a system for treating a disease or disorder of the ear, nose or throat of a human or animal subject, the system includes a guide catheter that is insertable into a head of the subject and has a substantially rigid shaft, a proximal opening, a distal opening and a lumen extending between the proximal opening and the distal opening. The system also includes a balloon catheter device as described above that is advanceable out of the distal opening of the guide catheter. The balloon catheter device also includes a guidewire lumen and the system includes a guidewire that is advanceable through the guidewire lumen. Also, the inflation lumen of the catheter shaft is sized so that, after the inflatable balloon has been inflated to a working diameter, the inflatable balloon will deflate in less than 5 seconds with application of negative pressure to the inflation lumen by a conventional balloon catheter inflation and deflation device.

The system may also include an irrigation catheter sized for advancement through the guide catheter into a paranasal sinus.

Furthermore, in an embodiment of a method for dilating a natural paranasal sinus ostium of a paranasal sinus of a patient, the method includes advancing a guide catheter into a head of a patient such that a distal end of the guide catheter is positioned within or near a natural paranasal sinus ostium of a paranasal sinus. Also, the method includes inserting an endoscope into the patient's head and advancing a balloon catheter through a lumen of the guide catheter such that a balloon of the catheter passes out of the distal end of the guide catheter. With the endoscope, a first distal shaft marker disposed on a shaft of the balloon catheter a first known distance from the balloon may be viewed, and also, a second distal shaft marker disposed on the shaft a second known distance from the balloon may be viewed. The method may include approximating a location of the balloon relative to the paranasal sinus ostium, using the first and second distal shaft marker and their known distances from the balloon. The balloon of the balloon catheter may be expanded to remodel or break bone underlying mucusa of the natural paranasal sinus ostium and dilate the ostium.

The method may also include viewing a first proximal shaft marker during the step of advancing the balloon catheter. When a distal end of the first proximal shaft marker enters a proximal end of the guide catheter a distal end of the balloon catheter shaft is located approximately at the distal end of the guide catheter. Also, when a proximal end of the distal shaft marker enters the proximal end of the guide catheter a proximal end of the balloon of the catheter is located approximately at the distal end of the guide catheter.

Further, the method includes viewing a second proximal shaft marker during the step of advancing the balloon catheter. The second proximal shaft marker is disposed distal to the first proximal shaft marker, and when the second proximal shaft marker is located approximately at the proximal end of the guide catheter, the distal end of the balloon catheter is located immediately proximal to a curve in the distal end of the guide catheter. The first distal shaft marker is located proximal to the balloon and the second distal shaft marker is located distal to the balloon.

In another embodiment, the first and second distal shaft markers are located proximal to the balloon. The first distal shaft marker may be located approximately one centimeter proximal to a proximal end of the balloon and the second distal shaft marker may be located approximately two centimeters proximal to the proximal end of the balloon. The method may also include viewing a third distal shaft marker located at the proximal end of the balloon.

The method may further include advancing a guidewire through the guide and through the ostium before advancing the balloon catheter. After the guidewire is in place, the balloon catheter is advanced over the guidewire and through the guide.

Also, the method may include removing the balloon catheter through the guide catheter and advancing an irrigation catheter through the guide catheter into the paranasal sinus. Once the irrigation catheter is in position, the sinus may be irrigated using the irrigation catheter.

Still further embodiments, aspects, features and details of the present invention will be understood upon reading of the detailed description and examples set forth herebelow.

BRIEF DESCRIPTION OF THE DRAWINGS

FIG. 1 is a side view of one embodiment of a dilation catheter with its dilator in an expanded configuration.

FIG. 1A is a cross sectional view through line 1A-1A of FIG. 1 with an enlarged break-out view of a portion thereof.

FIG. 1B is an enlarged side view of the dilator and distal end of the dilation catheter of FIG. 1.

FIG. 3A is a side view of another embodiment of a handle apparatus of the present invention.

FIG. 3B is a side view of yet another embodiment of a handle apparatus of the present invention.

FIG. 3C is a side view of yet another embodiment of a handle apparatus of the present invention.

FIG. 4 is an exploded, partial view of one embodiment of a dilation catheter system of the present invention including an optional handle apparatus.

FIG. 5 is a schematic diagram of one embodiment of a dilation catheter system of the present invention (without the optional handle apparatus) being used to dilate the ostium of a paranasal sinus.

FIG. 6 is a schematic diagram of one embodiment of a dilation catheter system of the present invention (with the optional handle apparatus) being used to dilate the ostium of a paranasal sinus.

FIG. 12 is a side view of another embodiment of a dilation catheter with its dilator in an expanded configuration.

FIG. 12A is a cross sectional view through line 12A-12A of FIG. 12.

FIG. 12B is an enlarged side view of the dilator and distal end of the dilation catheter of FIG. 12.

DETAILED DESCRIPTION

Figure 2:
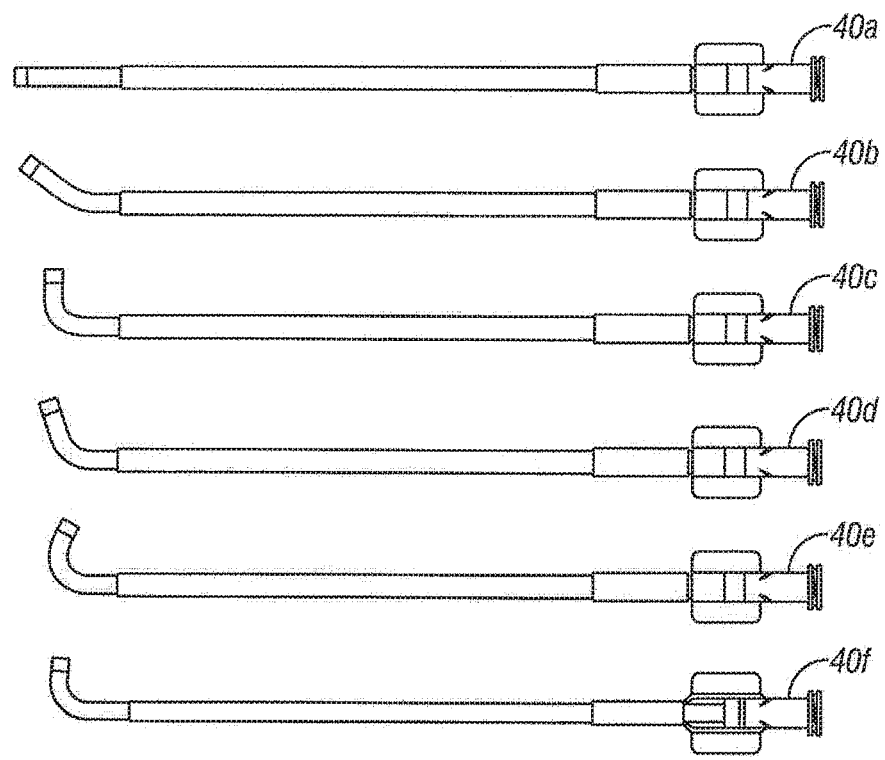
FIG. 2 shows a collection of transnasal guide catheters useable as components of the system of the present invention.

The following detailed description and the accompanying drawings are provided for the purpose of describing some, but not necessarily all, examples or embodiments of the invention. The contents of this detailed description and the accompanying drawings are exemplary in nature and do not limit the scope of the invention in any way.

A First Embodiment of a Dilation Catheter

FIGS. 1-1B show one example of a dilation catheter device 10 of the present invention with a guidewire GW operatively inserted therethrough. In this example, the dilation catheter device 10 comprises an elongate catheter shaft 12 having a proximal shaft section 12prox that is substantially rigid and a distal shaft section 12dist that is more flexible than the proximal shaft section 12prox. An expandable dilator, such as a balloon 14 or other suitable mechanical or non-inflational dilator, is mounted on the distal shaft section 12dist and a distal tip member 18 protrudes beyond the distal end of the balloon 14, as shown. Also, a proximal T hub 16 is attached to the proximal end of the proximal shaft section 12prox. This proximal T hub 16 has a proximal Luer connector 20 and a side arm 22 having a female Luer connector that extends substantially perpendicular to the longitudinal axis of the hub 16, as shown. When compared to a typical Y hub, the side arm 22 of this T hub is further away from the proximal Luer connector 20 and is oriented at a right angle to the proximal Luer connector 20. Thus, tubing connected to this perpendicular side arm 22 is less likely to obscure or block the proximal Luer connector 20 than in a typical Y hub and the operator is less likely to confuse the proximal Luer connector 20 with the Luer connector on the side arm 22.

Although, in the particular example shown in the drawings, the expandable dilator comprises a balloon 14, it is to be appreciated that various other types of expandable dilators such as expandable cages, struts and other expandable mechanical assemblies may be used as an alternative to a balloon 14. Some non-limiting examples of expandable dilators other than balloons have previously been described in parent U.S. patent application Ser. No. 11/355,512, issued as U.S. Pat. No. 8,894,614 on Nov. 25, 2014, Ser. No. 11/150,847, issued as U.S. Pat. No. 7,803,150 on Sep. 28, 2010, Ser. No. 10/944,270, published as U.S. Publication No. 2006/0004323 on Jan. 5, 2006, and Ser. No. 10/829,917, issued as U.S. Pat. No. 7,654,997 on Feb. 2, 2010, which are expressly incorporated herein by reference.

For use in teenage or adult humans, the overall length of the catheter shaft 12 may be in the range of about 15 cm to about 25 cm, the proximal shaft section 12prox may have a length in the range of about 10 cm to about 15 cm and the distal shaft section 12dist may have a length in the range of about 5 cm to about 10 cm. In the particular example shown in the drawings and described herein, the catheter shaft 12 has an overall length of 21.2 cm, the proximal shaft section 12prox being 12.5 cm in length and the distal shaft section 12dist being 8.7 cm in length. These optimal lengths of the proximal shaft section 12prox and distal shaft section 12dist have been arrived at based on a number of considerations, which will be discussed more fully herebelow in relation to the concurrent use of this dilation catheter 10 with a transnasal guide catheter.

As may be appreciated from the cross sectional view of FIG. 1A, the proximal shaft section 12prox comprises a rigid outer tube 30 a flexible middle tube 32 disposed substantially coaxially within the lumen of the rigid outer tube 30 and an inner tube 36 disposed substantially coaxially within the lumen of the middle tube 32. In this particular example, the outer tube 30 is formed of stainless steel hypotube having an outer diameter of 0.076 inches and an inner diameter of 0.068 inches. As an alternative to stainless steel hypotube, this outer tube 30 may be formed of rigid non-metallic material such as polyetheretherketone (PEEK) or other rigid plastics suitable for such application. Alternatively, other rigid reinforcing members may be used in, or in lieu of, the outer tube, such as wires (round, flat, square or of other cross section), partial tubes (e.g., arcs), etc. Also, in this particular example, the middle tube 32 is formed of Pebax having an inner diameter of 0.055 inches, an outer diameter of 0.065+/−0.003 inches. The inner tube 36 is formed of polyether block copolymer tubing (e.g., Pebax® Resin, Arkema, Inc., Philadelphia, Pa.) having an inner diameter of 0.038 inches, an outer diameter of 0.048 inches.

The outer tube 30 terminates at the end of the proximal shaft section 12prox. The middle tube 32 and inner tube 36 extend beyond the distal end of the outer tube 30, forming the distal shaft section 12dist.

As seen in the enlarged break-out segment of FIG. 1A, a polyether block copolymer film laminate 31 (e.g., Pebax® Resin, Arkema, Inc., Philadelphia, Pa.) is heat shrunk onto the outer surface of the catheter shaft 12 from the proximal hub 16 to the balloon 14. This laminate 31 provides a smooth outer surface and smoothes the step-down in diameter from the distal end of the proximal shaft section 12prox to the proximal end of the distal shaft section 12dist (i.e., it provides a smooth surface over the distal end of the outer tube 30 and the adjacent outer surface of the middle tube 32). The smooth step down may also be formed by an adhesive fillet. In other embodiments, the smooth step down may be formed by tapering or chamfering the structure of the distal end of the proximal shaft, eliminating the need for a laminate or adhesive.

The proximal end of the middle tube 32 extends into and is secured to the hub 16, distal to side arm Luer connector 22. The proximal end of the inner tube 36 extends into and is secured within hub 16, proximal to the side arm Luer connector 22 and in direct alignment and fluid communication with proximal Luer connector 20. The distal end of the middle tube 32 terminates within the balloon 14 and the proximal end of the dilator is secured to the outer surface of the middle tube. The distal end of the inner tube 36 also extends through the balloon 14 and protrudes distally beyond the balloon 14, forming the relatively flexible distal tip member 18 as shown in FIG. 1. The distal end of the balloon 14 is secured to the outer surface of the inner tube 36. In this manner, the inner tube lumen 38 extends through the entire catheter shaft 12 from the proximal Luer connector 20 through the distal tip 18 and may be used a guidewire lumen or as a working lumen for infusion of irrigation solution, medicaments, contrast media or other substances and/or for aspiration of blood, fluids or debris. Guidewires that may be advantageously used in conjunction with this dilation catheter 10 may have a length of 60 cm to 80 cm and may be either 0.014 inch or 0.035 inch, such as those commercially available as the Relieva® Sinus Guidewires (Acclarent, Inc., Menlo Park, Calif.) or sizes in between such as 0.018 inch, 0.020 inch, or 0.033 inch. Although the drawings show an over-the-wire catheter having a guidewire lumen that extends through the entire length of the catheter, it is to be appreciated that guidewire lumens extending less than the entire length of the catheter (e.g., rapid exchange guidewire lumens) may be used as an alternative to the over-the-wire lumen shown. Additionally, in some embodiments, rather than advancing the catheter over a guidewire, the catheter may be equipped with a fixed guidewire tip such as any of those described in U.S. patent application Ser. No. 11/438,090, issued as U.S. Pat. No. 8,951,225 on Feb. 10, 2015, entitled Catheters with Non-Removable Guide Members Useable for Treatment of Sinusitis, the entire disclosure of which is expressly incorporated herein by reference.

The inner tube lumen 38 may be lined or coated with a lubricious material to facilitate passages of the guidewire GW through that lumen 38. The diameter of the inner tube 36 may be changed to accommodate guidewires of different diameter. In the particular embodiment described, the inner tube lumen 38 is sized to receive a 0.035 inch diameter guidewire GW. The inner tube lumen 38 may be internally lined or coated with a 2% solution of linear polydimethylsiloxane (PDMS) (e.g., Dow Corning® 360 Medical Fluid, Dow Corning Corporation, Midland, Mich.) diluted in isopropyl alcohol or another silicone material (such as a 2% solution of Dow-Corning MDX4-4159 in isopropyl alcohol). The coating is cured at room temperature.

The luminal space 34 between the outer surface of the inner tube 36 and the inner surface of the middle tube 32 is in fluidic communication with the side arm Luer connector 22 and extends to the interior of the balloon 14. Thus, this luminal space 34 serves as the passageway through which inflation fluid is passes into and out of the balloon 14. The size of this luminal space 34 and the relatively short length of the catheter shaft 12 are optimized to minimize drag on inflation fluid passing through this luminal space 34 and allows for rapid deflation of the balloon 14. The clearance of 0.006 to 0.007 inches between the inner and outer member is desired for catheter length of 20-35 cm. The desired deflation time is 5-10 seconds and the deflation time is measured with application of negative pressure on the inflation/deflation lumen using a 20 cc inflation device that is filled with 10 cc contrast/saline mixture.

Balloon Construction and Coating

FIG. 1B shows details of the balloon 14. In this example, the balloon 14 is a noncompliant balloon formed of polyethylene teraphthalate (PET) film having a thickness of 0.8 mils. The balloon 14 has a cylindrical midregion 44 and tapered proximal and distal end regions 46prox and 46dist. The balloon 14 has an overall length of 2.6 cm. The cylindrical midregion 44 of the balloon 14 has a length of 16 mm (i.e., the "working length") and each tapered end region 46prox, 46dist has a length of 5 mm. The balloon 44 has a burst pressure of at least 14 to 16 atmospheres. The outer diameter of the balloon 14, when inflated to a pressure of 14 atmospheres, may be in the range of 5.0 mm to 5.5 mm. In this particular example, the balloon 14 is sized for dilation of the ostia of paranasal sinuses and such balloon 14 is offered in sizes having outer diameters of 5 mm or 7 mm when inflated to a pressure of 14 atmospheres. Dilation catheters 10 having the 5 mm diameter balloon 14 may be more suitable for use in subjects of small body size while dilation catheters 10 having the 7 mm diameter balloon 14 may be more suitable for use in subjects having a large body size. Smaller or larger balloons may be used for dilating structures other than the ostia of paranasal sinuses (e.g., Eustachian tube or nasolacrimal duct dilations). Larger balloons and higher pressures may be used for dilating revision patients (i.e., patients who have had prior ostial dilations or who's ostia have been previously modified by surgery).

The tapered end regions 46prox, 46dist are tapered at angle A relative to the longitudinal axis LA of the catheter shaft 12 on which the balloon 14 is mounted. This angle of taper A may be in the range of about 10 degrees to about 30 degrees. In the particular example shown in the drawings, such angle of taper A is 20 degrees. This 20 degree angle of taper provides improved transition from balloon working length to the necks, lower profile, improved crossing, improved track, easier withdrawal in the sinus guide after balloon inflation. It also provides optimal performance with minimum increase of overall balloon length.

In some embodiments, it may be desirable for the relatively stiff proximal shaft portion 12prox to extend all the way to or near the proximal end of the balloon 14 or other dilator. Such catheter having a rigid shaft from its proximal end to or near the dilator may be advanced directly into the sphenoid sinus ostium with or without the use of a guide catheter. In some embodiments, the proximal end of the balloon 14 could be bonded to the relatively rigid proximal shaft portion 12prox. Such a construction would allow the flexible distal tip 18 to track turns in the anatomy and may be useable to dilate certain passageways (e.g., the sphenoid sinus ostium) without disrupting the normal anatomy. Additionally, embodiments with relatively short distal shaft sections (e.g., 1-2 cm beyond the distal end of the rigid proximal shaft portion are particularly suitable for dilating the Ostia of frontal sinuses. Also, in some embodiments, the proximal shaft section 12prox may be malleable so that it may be shaped (e.g., bent or formed to a desire curve or multi-curvate shape) to facilitate access to any desired passageways or locations.

Endoscopically Visible Markers and Anti-Glare Coatings

An additional visible marker 19 may optionally be formed on the proximal end of the balloon 14 and/or on the distal shaft portion 12dist, such as at the location where the proximal end of the balloon 14 is bonded to the distal shaft portion 12dist.

These visible markers 19, 24, 26 are preferably of a color (e.g., black or blue) that contrasts with the pink color of the nasal mucosa so as to be easily visible within the nose. The optional marker 19 on the proximal end of the balloon 14 allows the operator to endoscopically view the proximal end of the balloon even when the remainder of the balloon is within the ostium of a paranasal sinus. The other visible markers 24, 26 formed on the proximal shaft are specifically designed for use in conjunction with a guide catheter as will be discussed in detail herebelow.

In some cases, endoscopic images obtained of the markers or other portions of the guidewires GW, guide catheter 40a-40f or dilation catheter 10 may have areas of glare which can obscure visualization of certain portions of the markers or devices during performance of the procedure. To minimize such glare, an anti-glare (e.g., anti-reflective) treatment or coating may be applied to all or part of the sinus guide catheter 40a-40f, sinus guidewire GW and/or dilation catheter 10. Such anti-glare treatment could be applied by etching or sand-blasting and therefore does not add profile to the device. Such anti-glare coating could be applied by dip or spray coating and is very thin. The treatment or coating does not change the mechanical or functional properties of these devices. It may be selectively applied. For example, a black polytetrafluoroethylene (PTFE) coating on the sinus guidewire GW may provide good anti-reflective characteristics. Some of the commercially available anti-glare or anti-reflective coating can be applied. In some embodiments, an anti-glare surface treatment (e.g., roughening, etching, etc.) may be used or an anti-glare component such as a sheath, ring, paint, etc. may be used.

The advantages and benefits of including visible markers and/or the anti-glare coating include, improved endoscopic visualization, safer and easier performance of the procedure, reduced balloon burst or damage to critical structures, accuracy of placement of devices and reduced fluoroscopy time or elimination of fluoroscopy.

Dilation Catheter/Guide Catheter System

FIG. 2 shows a series of sinus guide catheters 40a-40f that may be used in conjunction with the dilation catheter 10. These guide catheters 40a-40f are substantially rigid and each has a preset distal curve of 0 degrees (40a), 30 degrees (40b), 90 degrees (40d), 70 degrees (40c) or 110 degrees (40e and 40f). Different curvatures are useable to access the ostia of different sinuses. For example, a 70 degree guide is typically used to access the ostium of a frontal sinus, a 90 or 110 degree guide is typically used to access the ostium of a maxillary sinus, etc. Each of these guide catheters 40a-40f has a length of 12.7 cm. These sinus guide catheters are described in parent United States patent application Ser. Nos. and are now commercially available as Relieva® sinus guide catheters from Acclarent, Inc., Menlo Park, Calif.

FIG. 5 shows a system comprising a guide catheter 40c having a 90 degree curve formed therein in combination with a dilation catheter 10 shown in FIG. 1. In optimizing the relative lengths of the proximal shaft section 12prox and distal shaft section 12dist, applicants have determined that, even the maximum distance that the distal end of the dilation catheter of this example is required travel beyond the distal end of the guide catheter 40a-40c is approximately 2.5 cm. However, it will be appreciated that this is just one example. For other application, travel beyond 2.5 cm may be desirable or necessary. Also, it is desirable for the entirety of the more flexible distal shaft section 12dist to be advanceable into the guide catheter 40a-40f proximal to any curve formed in the guide catheter. With these objectives in mind, the example of the dilation catheter 10 shown in the drawings has a shaft that is about 20 cm in length, with the proximal shaft section 12prox being 11.3 cm in length and the distal shaft section 12dist being 8.7 cm in length. Thus, prior to or during the procedure, the entire distal shaft section 12dist of the dilation catheter 10 may be initially advanced into the rigid guide catheter 40c without the distal portion of the dilation catheter 10 passing through the curve of the guide catheter 40c and with only a portion of the rigid proximal shaft section 12prox of the dilation catheter 10 protruding out of the proximal end of the guide catheter 40c. To facilitate such positioning of the dilation catheter 10 within the guide catheter 40d, a first shaft marker 26 is provided on the proximal shaft section 12prox of the dilation catheter shaft 12. The distal edge of this first shaft marker 26 is 2.7 cm proximal to the distal end of the proximal shaft section 12prox and 11.4 cm from the distal end of the distal tip member 18. If the operator advances the dilation catheter 10 into the guide catheter 40c until the distal edge of the first shaft marker 26 is flush with the proximal end of the guide catheter 40c, the entire distal shaft portion 12dist as well as the distal-most 3 cm of the proximal shaft portion 12prox will be housed within the guide catheter 40c such that the distal end of the dilation catheter 10 is located proximal to the curve formed near the distal end of the guide catheter 40c. Such positioning of the dilation catheter 10 within the guide catheter 40c provides a guide catheter/dilation catheter assembly that is substantially rigid from the proximal hub 16 of the dilation catheter 10 to the distal end of the guide catheter 40c. As a result, the operator may hold or support the entire assembly by grasping or supporting just one location on either the dilation catheter 10 or guide catheter 40d. For example, the user may hold or support the entire assembly by using his fingers to grasp or support either the proximal hub of the guide catheter 40c, the proximal hub 16 of the dilation catheter 10 or somewhere on the proximal shaft section 12prox of the dilation catheter or on the shaft of the guide catheter 40c. Such rigidity also substantially eliminates the potential for the exteriorized portion of the dilation catheter 10 to droop down onto the subject's chest or onto the adjacent operating table.

As explained above, in this example, the rigid proximal shaft segment 12prox of the dilation catheter 10 is 11.3 cm in length and the guide catheter 40d is 12.7 cm in length. Thus, when inserted into the subject's body, the overall length of the portion of the system that remains exteriorized (e.g., the proximal part of the guide catheter 10 extending out of the subject's nose and the proximal part of the dilation catheter 10 extending out of the proximal end of the guide catheter 40c) is not only rigid, but sufficiently short (e.g., typically less than 9 cm) to be easily manageable and capable of being held or supported by a single hand of the operator, thereby allowing the operator's other hand to be used for other purposes, such as for advancing/retracting the guidewire GW or advancing/retracting the dilation catheter 10 in the manner described herebelow in connection with FIGS. 9-11.

The second shaft marker 24 correlates to the position of the balloon. If the dilation catheter 10 is advanced to a position where the distal edge of the second shaft marker 24 is flush with the proximal end of the guide catheter 10, the distal tip of the balloon catheter will be flush with the distal tip of the guide catheter 40d. When the proximal edge of the second shaft marker 24 is flush with the proximal end of the guide catheter 10, the entire balloon 14 will have advanced out of the distal end of the guide catheter 40d and the operator will know that it is safe to inflate the balloon. Typically, as seen in FIG. 5, the balloon 14 is advanced some distance out of the distal end of the guide catheter 40d until the balloon 14 is positioned within the sinus ostium SO or other passageway to be dilated. As seen in the enlarged view of the balloon 14 shown in FIG. 1B, proximal and distal radiographic markers 40, 42 are provided on the catheter at either end of the cylindrical segment 44 of the balloon. A C arm fluoroscope may be positioned and used to image those proximal and distal markers 40, 42 as well as the sinus ostium SO and the position of the dilation catheter 10 may be adjusted as needed until the sinus ostium SO is midway between the proximal and distal radiographic markers 40, 42. Thereafter, an inflator 50 attached to the side arm Luer connector 22 may be used to inflate the balloon 14, thereby dilating the sinus ostium SO as shown in FIG. 5. In keeping with the operator's ability to use a single hand to hold or support the exteriorized portion of the system, the inflator 50 may be attached to the side arm Luer connector 22 in advance and may be controlled by a foot pedal which is actuated by the operator's foot.

In some applications of the system shown in FIG. 5, an endoscope may be placed in the nose and used to view all or part of the procedure. Because the exteriorized portion of the system is substantially rigid and is typically less than 15 cm in length, the operator may use a single hand to hold the endoscope as well as the dilation catheter/guide catheter system. Alternatively, a scope holder may be used to hold the endoscope in a fixed position while the operator positions and uses the system seen in FIG. 5. Alternatively, an optional handle may be used as shown in FIGS. 3-4, 6 and 8A-8B and described below.

Optionally, a member 61 may be attached to the guidewire. Such member may serve to prevent the dilation catheter 10 and/or guide catheter 40a-40f from inadvertently sliding off of the proximal end of the guidewire. Also, such member 61 may limit the length of guidewire GW that may be advanced through the dilation catheter 10. This will prevent the operator from advancing too much of the guidewire GW into the subject's sinus, as may injure or damage the mucosa lining the sinus cavity. In some embodiments, this member 61 may be a standard guidewire torquer of the type commercially available and well known in the fields of interventional cardiology and/or radiology. One example of a commercially available guidewire torquer that is useable in this application is a two part torquer available as Part No. 97333 from Qosina, Corp., Edgewood, N.Y.

Figure 7A:
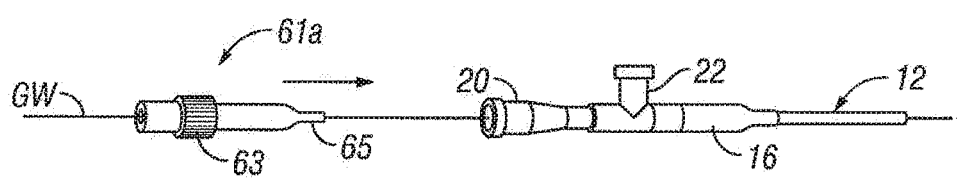
FIG. 7A shows a partial view of the system of FIG. 5 including a guidewire stop/connector apparatus of the present invention mounted on the guidewire prior to advancement of the guidewire.
Figure 7B:
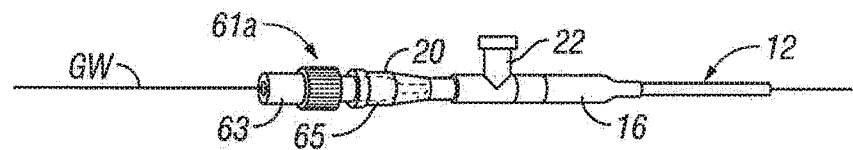
FIG. 7B shows a partial view of the system of FIG. 5 including a guidewire stop/connector apparatus of the present invention mounted on the guidewire and engaged with the hub of the dilation catheter following advancement of the guidewire.

Alternatively, the member 61 may comprise a guidewire stop/connector apparatus 61a as shown in FIGS. 7A-7B. This stop/connector apparatus 61a comprises a rigid plastic body 63 having a lumen extending therethrough and a tapered elastomeric tube member 65 on its distal end. The stop/connector apparatus 61a is advanced over the guidewire GW to the desired location. The inner diameter of the tapered elastomeric tube member 65 fits snuggly on the guidewire thereby holding the stop/connector apparatus 61a as seen in FIG. 7A. The guidewire GW is subsequently advanced through the dilation catheter 10 until the tapered elastomeric tube member 65 is received within and frictionally engages the proximal female Luer connector 20 on the hub of the dilation catheter, as shown in FIG. 7B. This limits advancement of the guidewire GW and also frictionally locks the guidewire GW to the dilation catheter 10 so that the operator may move both the guidewire GW and the dilation catheter 10 as a unit. If the operator decides to advance more of the guidewire into the sinus, the operator may grasp and move the stop/connector apparatus 61a by applying sufficient force to overcome the frictional engagement between the stop/connector apparatus 61a and the guidewire GW and/or between the stop/connector apparatus 61a and the guide catheter hub. The force required to overcome such frictional engagements will preferably be greater than the forces that would normally result from routine movement and use of the system, thereby allowing the stop/connector apparatus 61a to perform its locking function while still allowing the location of the stop/connector apparatus 61a to be volitionally adjusted by the operator when necessary.

Alternatively or additionally, if desired, another stop/connector apparatus 61a of larger size (or another suitable locking apparatus such as a Touhy-Borst valve) may be mounted on the rigid proximal shaft section 21prox of the dilation catheter 10 and received within the proximal end of the guide catheter 40a-f to limit the advancement of the dilation catheter 10 through the guide catheter 40a-f and to frictionally lock the dilation catheter 10 to the guide catheter 40a-f in the same manner.

Dilation Catheter/Guide Catheter System with Optional Handle

Figure 3:
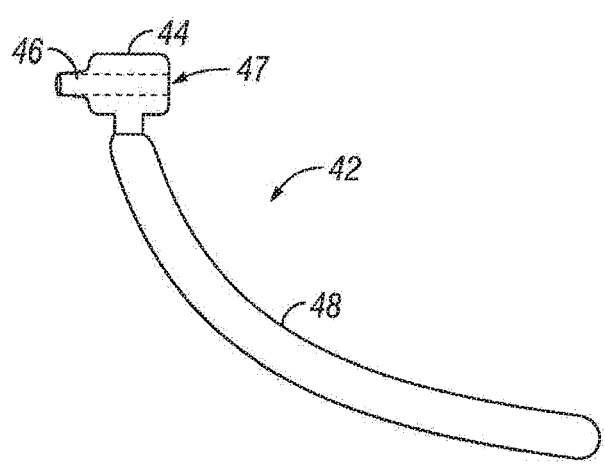
FIG. 3 is a side view of one embodiment of a handle apparatus of the present invention.

FIG. 3 shows an optional handle 42 that may be attached to the guide catheter 40a-40d to facilitate single-handed holding of the guide catheter/dilation catheter system as well as an endoscope (or other device). The handle shown in FIG. 3 comprises a rigid head 44 having a male Luer fitting on one end, a lumen 47 extending therethrough and a handle member 48 extending therefrom. As seen in the exploded view of FIG. 4, the male Luer fitting 46 may be inserted into the proximal end of the guide catheter 40c and the guidewire GW and guide catheter 10 may then be inserted through the lumen 47 of the handle head 44 and through the guide catheter. The handle head 44 may be clear or transparent so that the operator may view the shaft markers 24, 26 on the dilation catheter shaft 12 as the dilation catheter 10 is advanced through the handle head 44. Alternatively, the locations of the shaft markers 24, 26 may be adjusted on the catheter shaft 12 to take into account the additional guide length added by the handle head 44. The handle member 48 is preferably about the size of a standard ink pen and may be conveniently grasped by a human hand. The handle member 48 may have a roughened or elastomeric surface to facilitate gripping by a gloved hand and to deter slippage of the handle from the operator's grip. The handle member 48 may be shapeable (e.g., malleable or bendable) to allow the operator to adjust the shape and/or angle of the handle relative to the shaft of the guide catheter 40c. In some embodiments, the handle member 48 may be pre-shaped to accommodate a typical user and allow fine tuning by individual user. Also, in some embodiments, the handle member 48 may have foam or other material on its surface to facilitate grip. The handle member 48 may have various different cross sectional profiles (e.g., round, oval, 3 sided, 4 sided, 5 sided, 6 sided, etc.) The handle 48 serves to facilitate grip and control to manipulate the dilation catheter along with a separate device (e.g., an endoscope or other tool) without having to use second hand. In this manner, the user may adjust rotation of a guide catheter while observing under endoscope (all with one hand) and use other hand to advance and place the guidewire or other device. Also, in some embodiments, the handle member 48 may include finger loop(s) for easier to translate handle/device attached up/down relative to other device held (e.g. scope) without need for other hand to adjust. Also, in some embodiments, a pinch valve or hole can be strategically placed in handle 48 to actuate/allow control of suction or fluid delivery via handle device (e.g., the user may pinch the handle with fingers to restrict flow through handle) or the handle 48 may have a suction hole where the user must cover the suction hole to actuate suction through the optional handle 42.

Alternative embodiments of the handle are shown in FIGS. 3A, 3B and 3C. FIG. 3A shows a handle 42a which is similar to that seen in FIG. 3, but wherein a fluid channel 52 extends from the lumen 47 downwardly through the head 44a and through the handle member 48a. A one way valve 50 is disposed within the lumen 47, proximal to the location where the fluid channel 52 meets the lumen 47. An irrigation and/or suction tube 54 may be attached to the handle member 48a to infuse fluid through or suction fluid and debris through the fluid channel 52. The one way valve will ensure that fluid infused or aspirated through the fluid channel 52 of the handle 42a will not escape out of the proximal opening of the lumen 47. However, this one way valve 50 does allow the guidewire GW and dilation catheter 10 to be inserted through the lumen 47, when desired. The one way valve may provide the additional benefit of maintaining the position of the guidewire or dilatation catheter when it is inserted in the guide handle. It will be appreciated that other types of valves other than a one-way valve may be used as an alternative (e.g., Touhy rotating type valve, slide to compress valve, etc.) Or, some embodiments may have just a valve and a thumb/finger hole to control the suction force as described above.

FIG. 3B shows another embodiment of an optional handle 42b comprising a clear or transparent rigid head 44b having a male Luer fitting 46b on one end and a lumen 47 extending therethrough. In this embodiment, the handle member 48b is formed of a series or pivotally interconnected units 56 which allows the handle member 48b to be conveniently formed into various shapes as desired by the operator.

FIG. 3C shows yet another handle 42c comprising a malleable or rigid handle 48c that is substantially the same as that shown in FIG. 3, but wherein a clip 58 is provided at the top end of the handle member 48c to clip the handle member 48c onto the shaft of the guide catheter 40c rather than inserting into the proximal end of the guide catheter.

Figure 8A:
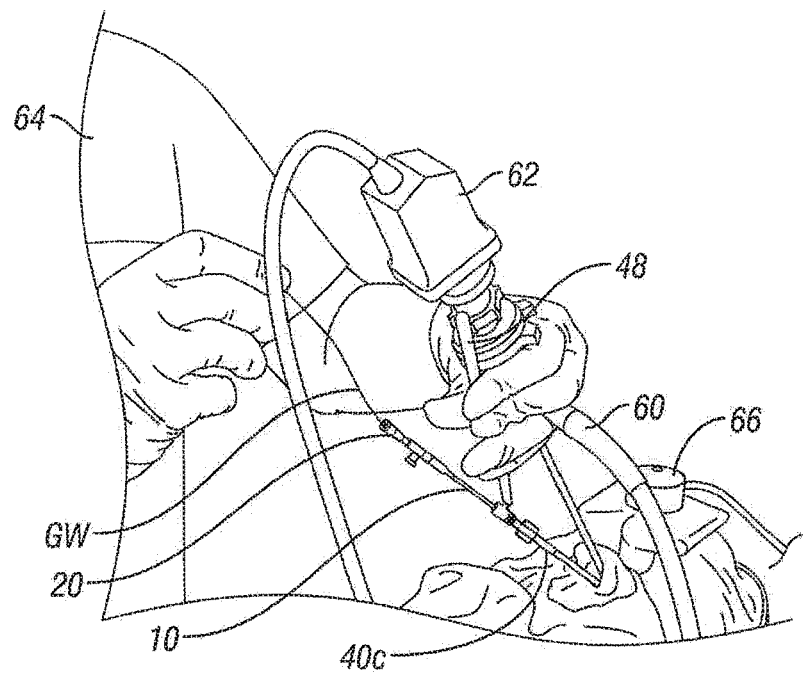
FIG. 8A shows the dilation catheter system of FIG. 6 and an endoscope being held by one hand of the operator while the operator's other hand is being used to advance the guidewire of the system into a paranasal sinus.
Figure 8B:
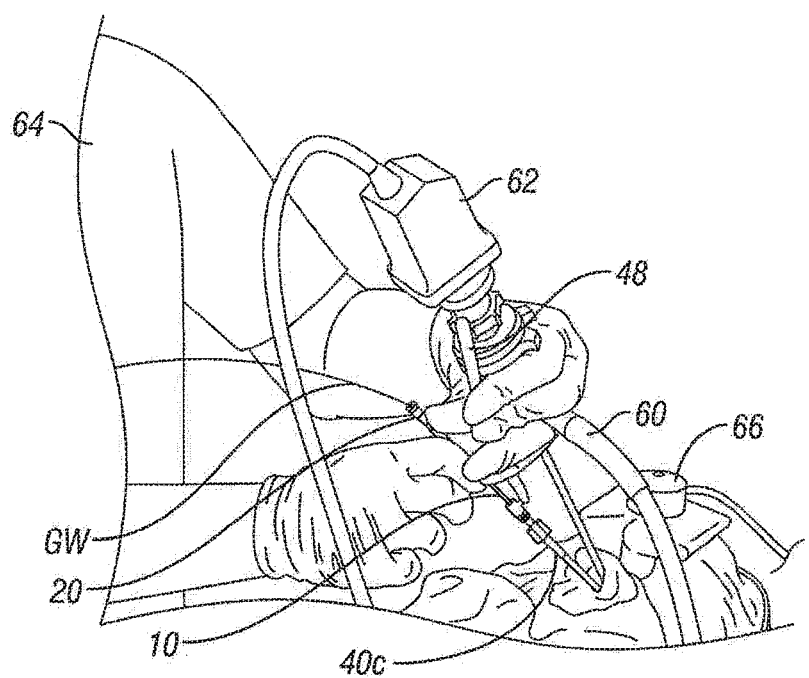
FIG. 8B shows the dilation catheter system of FIG. 6 and an endoscope being held by one hand of the operator while the operator's other hand is being used to advance the dilation catheter so that its dilator becomes positioned within the ostium of the paranasal sinus.

FIG. 6 shows the system of FIG. 5 with the inclusion of the optional handle 42 on the proximal end of the guide catheter 40c. FIGS. 8A and 8B show examples of how a handle 42 may be used to facilitate concurrent holding of an endoscope as well as the guide catheter (or guide catheter/dilation catheter assembly) by a single hand (i.e., the "scope hand") of the operator. With reference to FIGS. 5 and 8A-8B, the handle head 44 may initially be loosely inserted into the proximal hub of the guide catheter 40c. The camera 62 and light cable 66 are attached to the endoscope 60. While grasping the endoscope 60 in the manner shown in FIG. 8A, the operator may rotate the handle 42 relative to the guide catheter 40c to introduce the handle member 48 to the operator's scope hand. Alternatively, the handle member 48 could be grasped by the operator's scope hand along with the endoscope 60 upon initial introduction. When positioning of the endoscope 60 and guide catheter 40c have been achieved, the operators other hand is used to push the male Luer fitting 46 of the handle 42 firmly into the female Luer fitting on the proximal end of the guide catheter 40c, thereby locking the handle 42 to the guide catheter 40c. Thereafter, the operator's other hand is used to manipulate the guidewire GW and dilation catheter 10. In this manner, the operator may maintain continuous endoscopic visualization via the endoscope 60 while using the guidewire GW and dilation catheter to dilate the ostium of a paranasal sinus or other passageway within the ear, nose or throat. As explained in more detail below, positioning of the guidewire GW and/or balloon 14 (or other dilator) may be confirmed using fluoroscopy, trans-illumination or other techniques in addition to visualization via the endoscope 60. The guide handle 42 may also be used to allow the operator to hold or support the guide catheter 40c (or the entire guide catheter/dilation catheter system) while keeping his hand a spaced distance away from the guide catheter shaft so as to avoid radiation exposure to his hand during use of the fluoroscope.

In embodiments where the handle member 48 is shapeable (e.g., malleable or bendable) the shape of the handle member 48 may be modified one or more times prior to or during the procedure to facilitate comfortable grasping of the handle by the operator's scope hand and/or to adjust the position or angle of the endoscope relative to the guide catheter. In this regard, in FIG. 8A, the handle member 48 is bent to a shape that results in a first angle A between the shaft of the guide catheter 40c and the endoscope 60, and the operator's other hand is being used to advance the guidewire GW through the lumen of the dilation catheter 10. In FIG. 8A, the handle has been modified to a different shape that results in a lesser angle A between the shaft of the guide catheter 40c and the endoscope 60, and the operator's other hand is being used to advance the dilation catheter 10 through the lumen of the guide catheter 40c.

The optional handle 42 may also be useful with other dilation catheters and other trans-nasal devices described in any or all of the parent applications of which this application is a continuation-in-part and/or those currently available commercially under the trademark Relieva from Acclarent, Inc., Menlo Park, Calif.

Figure 10:
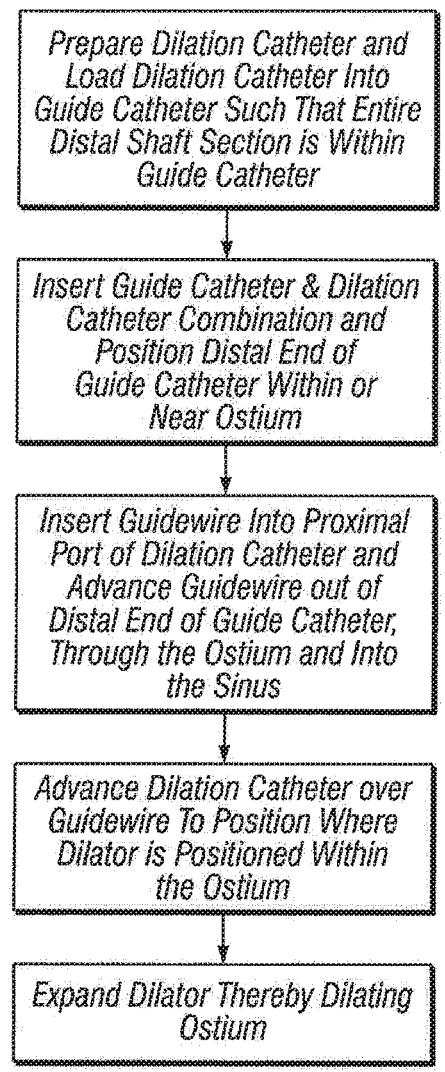
FIG. 10 is a flow diagram showing steps in another method for using a dilation catheter system of the present invention.
Figure 11:
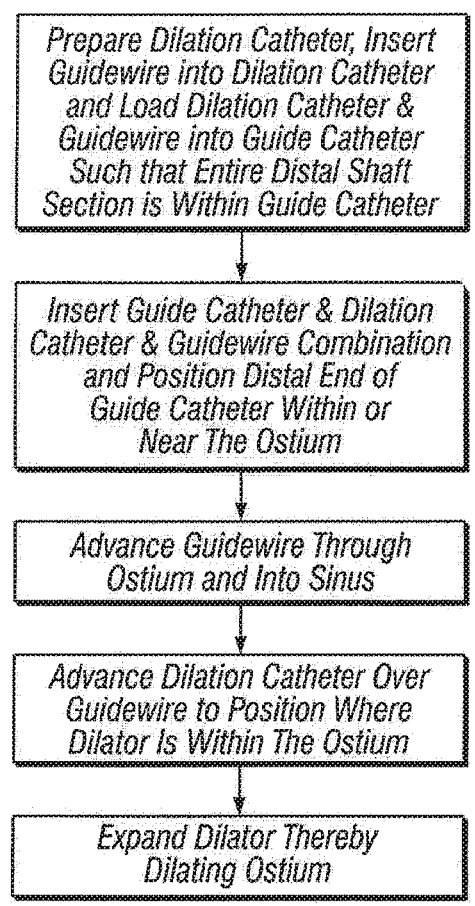
FIG. 11 is a flow diagram showing steps in yet another method for using a dilation catheter system of the present invention.

In some applications, the handle 42 may be designed to connect by way of a unique or proprietary connector to the guide catheter or other device. Or, in some embodiments, the handle 42 may be pre-attached, integrally formed with or otherwise designed as a part or portion of the guide catheter or other device. In embodiments where the handle 42 is not detachable from the guide catheter or other device, it may nonetheless be rotatable and/or lockable in a desire position Modes of Use of the System FIGS. 9-11 are flow diagrams describing three (3) modes of use by which the system of the present invention may be used to dilate the ostium of a paranasal sinus.

Mode 1—Inserting Guide Catheter, Guidewire and Dilation Catheter Separately

Figure 9:
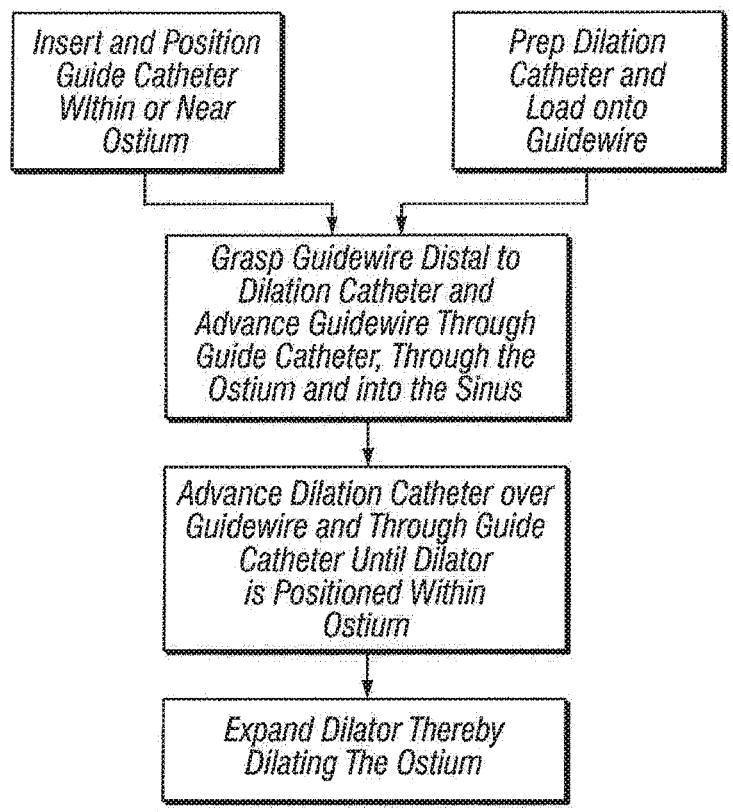
FIG. 9 is a flow diagram showing steps in one method for using a dilation catheter system of the present invention.

In the example of FIG. 9, the dilation catheter 10 is prepared for use separately from the guide catheter 40a-40f. The guide catheter 40a-40f is initially inserted (along with an endoscope 60) and is advanced to a position that is within or near the ostium to be dilated. An endoscope 60 is used to view the advancement and positioning of the guide catheter 40a-40f and fluoroscopy may also be used to verify that the guide catheter is properly positioned near or within the ostium. Optionally, a handle 42 may be attached to the guide catheter 40a-40f as described above or the operator may simply grasp the guide catheter 40a-40f as well as the endoscope 60 with the scope hand, thus leaving the operator's other hand free to be used for subsequent handling and manipulation of the other devices used in this procedure. Alternatively, a scope holder or assistant may be used to hold the endoscope 60 in the desired position thus freeing both of the operator's hands for handling and manipulation of the other devices.

After the guide catheter 40a-40f has been positioned, the operator will insert the distal end of the guidewire into the proximal end of the guide catheter 40a-40d and will advance the guidewire GW through the guide catheter 40a-40d such that a distal portion of the guidewire GW passes through the sinus ostium and becomes coiled within the sinus cavity. Fluoroscopy (or any other suitable technique) may be used to verify that the guidewire has become coiled within the intended sinus cavity.

Thereafter, the proximal end of the guidewire GW is inserted into the distal end of the dilation catheter 10 and the dilation catheter 10 (with its balloon 14 or other dilator in its non-expanded state) is advanced over the guidewire and through the guide catheter 40a-40d to a position where the dilator 14 is positioned within the sinus ostium. The endoscope 60 may be used to view the advancement and positioning of the dilation catheter 10. Although the distal portion of the balloon 14 or other dilator will be within the sinus and out of the field of view of the endoscope 60, the endoscope 60 may be used to view the proximal end of the balloon 14 or other dilator and/or the optional marker 19 (if present) on the proximal end of the balloon 14 or other dilator. Fluoroscopy may be used to image the radiographic markers 40, 42 and the ostium to confirm that the midregion 44 of the balloon 14 (or the appropriate portion of any other type of dilator) is positioned within the ostium.

After the balloon 14 or other dilator has been positioned within the ostium, the balloon is inflated (or the other dilator is expanded) thereby dilating the ostium.

The balloon is then deflated (or the dilator is returned to its non-expanded state) and the successful dilation of the ostium may be confirmed visually using the endoscope 60 and/or radiographically using a fluoroscope.

Thereafter, the dilation catheter 10, guidewire GW and guide catheter 40a-40f are removed.

Mode 2—Preloading Dilation Catheter into Guide Catheter then

Inserting Guidewire Separately

In the example of FIG. 10, the dilation catheter 10 is prepared for use and is pre-inserted into the guide catheter 40a-40f to a position where the first shaft marker 24 is flush with the proximal end of the guide catheter. When so positioned all of the flexible distal shaft portion 12dist and a bit of the rigid proximal shaft portion 12prox will be within the guide catheter 40a-40f.

Thereafter, the guide catheter 40a-40f in combination with the pre-inserted dilation catheter 10 is inserted transnasally (along with an endoscope 60) and is advanced to a position that is within or near the ostium to be dilated. The endoscope 60 is used to view the advancement and positioning of the guide catheter 40a-40f and fluoroscopy may also be used to verify that the guide catheter is properly positioned near or within the ostium. Optionally, a handle 42 may be attached to the guide catheter 40a-40f as described above or the operator may simply grasp the guide catheter 40a-40f as well as the endoscope 60 with the scope hand, thus leaving the operator's other hand free to be used for subsequent handling and manipulation of the other devices used in this procedure. Alternatively, a scope holder or assistant may be used to hold the endoscope 60 in the desired position thus freeing both of the operator's hands for handling and manipulation of the other devices.

After the guide catheter 40a-40f and pre-inserted dilation catheter 10 have been positioned, the operator will insert the distal end of the guidewire into the proximal Luer 20 of the dilation catheter 10 and will advance the guidewire GW through the dilation catheter 10, out of the distal end of the guide catheter 40a-40d and through the sinus ostium, causing a distal portion of the guidewire to become coiled within the sinus cavity. Fluoroscopy (or any other suitable technique) may be used to verify that the guidewire has become coiled within the intended sinus cavity.

Thereafter, the dilation catheter 10 (with its balloon 14 or other dilator still in its non-expanded state) is advanced over the guidewire GW to a position where the balloon 14 or other dilator is positioned within the sinus ostium. The endoscope 60 may be used to view the advancement and positioning of the dilation catheter. Although the distal portion of the balloon 14 or other dilator will be within the sinus and out of the field of view of the endoscope 60, the endoscope 60 may be used to view the proximal end of the balloon 14 or other dilator and/or the optional marker 19 (if present) on the proximal end of the balloon 14 or other dilator. Fluoroscopy may be used to image the radiographic markers 40, 42 and the ostium to confirm that the midregion 44 of the balloon 14 (or the appropriate portion of any other type of dilator) is positioned within the ostium.

After the balloon 14 or other dilator has been positioned within the ostium, the balloon is inflated (or the other dilator is expanded) thereby dilating the ostium.

The balloon is then deflated (or the dilator is returned to its non-expanded state) and the successful dilation of the ostium may be confirmed visually using the endoscope 60 and/or radiographically using a fluoroscope.

Thereafter, the dilation catheter 10, guidewire GW and guide catheter 40a-40f are removed.

Mode 3—Preloading Guidewire and Dilation Catheter into Guide Catheter

In the example of FIG. 11, the dilation catheter 10 is prepared for use and the distal end of the guidewire is pre-inserted into the proximal Luer 20 of the dilation catheter 10 and advanced to a position where the distal end of the guidewire is within protruding just slightly out of the distal end of the dilation catheter 10. The dilation catheter 10, with the pre-inserted guidewire GW, is pre-inserted into the guide catheter 40a-40f and advanced to a position where the first shaft marker 24 is flush with the proximal end of the guide catheter. When so positioned all of the flexible distal shaft portion 12dist and a bit of the rigid proximal shaft portion 12prox will be within the guide catheter 40a-40f.

Thereafter, the guide catheter 40a-40f with the dilation catheter 10 and guidewire pre-inserted therein is inserted through a nostril (along with an endoscope 60) and is advanced to a position that is within or near the ostium to be dilated. The endoscope 60 is used to view the advancement and positioning of the guide catheter 40a-40f and fluoroscopy may also be used to verify that the guide catheter is properly positioned near or within the ostium. Optionally, a handle 42 may be attached to the guide catheter 40a-40f as described above or the operator may simply grasp the guide catheter 40a-40f as well as the endoscope 60 with the scope hand, thus leaving the operator's other hand free to be used for subsequent handling and manipulation of the other devices used in this procedure. Alternatively, a scope holder or assistant may be used to hold the endoscope 60 in the desired position thus freeing both of the operator's hands for handling and manipulation of the other devices.

After the guide catheter 40a-40f and pre-inserted dilation catheter 10 and guidewire GW have been positioned, the operator will advance the guidewire out of the distal end of the guide catheter 40a-40f and through sinus ostium, causing a distal portion of the guidewire to become coiled within the sinus cavity. Fluoroscopy (or any other suitable technique) may be used to verify that the guidewire has become coiled within the intended sinus cavity.

Thereafter, the dilation catheter 10 (with its balloon 14 or other dilator still in its non-expanded state) is advanced over the guidewire GW to a position where the balloon 14 or other dilator is positioned within the sinus ostium. The endoscope 60 may be used to view the advancement and positioning of the dilation catheter. Although the distal portion of the balloon 14 or other dilator will be within the sinus and out of the field of view of the endoscope 60, the endoscope 60 may be used to view the proximal end of the balloon 14 or other dilator and/or the optional marker 19 (if present) on the proximal end of the balloon 14 or other dilator. Fluoroscopy may be used to image the radiographic markers 40, 42 and the ostium to confirm that the midregion 44 of the balloon 14 (or the appropriate portion of any other type of dilator) is positioned within the ostium.

After the balloon 14 or other dilator has been positioned within the ostium, the balloon is inflated (or the other dilator is expanded) thereby dilating the ostium.

The balloon is then deflated (or the dilator is returned to its non-expanded state) and the successful dilation of the ostium may be confirmed visually using the endoscope 60 and/or radiographically using a fluoroscope.

Thereafter, the dilation catheter 10, guidewire GW and guide catheter 40a-40f are removed.

Although the above described examples refer to use of a guide catheter 40a-40d and/or guidewire GW to guide the advancement of the dilation catheter 10 to its intended position within the ear, nose or throat, it is to be appreciated that in some subjects and/or in some applications, the dilation catheter may be advanceable or maneuverable to its intended position without the use of a guide catheter 40a-40f and/or guidewire GW. For example, in some subjects, the dilation catheter 10 may be advanced into the sphenoid sinus ostium without the use of a guidewire GW or guide catheter 40a-40d. Alternatively the flexible balloon portion may be manipulated with forceps to enable insertion in the ostium. Similar techniques may apply to access of the frontal and maxillary ostium.

The fact that the system described herein includes a guide catheter 40a-40f that is separate from the dilation catheter 10 has certain advantages. For example, by having two separate devices, the operator has separate control of the guide placement and may, in some cases, elect not to actually advance the guide into the ostium or recess before the ostium. Rather, the operator may in some instances elect to maneuver the guide catheter 40a-40f to a position that is close to (e.g., aligned with) but not within the ostium or recess, and may then advanced just the relatively flexible dilation catheter 10 into the ostium or recess. This may avoid damage tissue, bone or other anatomical structures. Thus, the use of a guide that is separate from the dilation catheter allows flexibility of positioning and potentially less trauma than where a single rigid device (e.g., a rigid shafted dilation catheter) must be navigated to the desired location and then actually inserted into the ostium or other passageway to be dilated.

Alternative Embodiment of a Balloon Dilation Catheter

FIGS. 12-12B show another example of a balloon dilation catheter device 70. In this embodiment, the dilation catheter device 70 includes an elongate catheter shaft 72 having a proximal shaft section 72prox that is substantially rigid and a distal shaft section 72dist that is more flexible than the proximal shaft section 72prox. An expandable dilator, such as a balloon 74, or other suitable mechanical or non-inflational dilator, is mounted on the distal shaft section 72dist, and a distal tip member 78 protrudes beyond the distal end of the balloon 74, as shown. Also, a proximal T hub 76 is attached to the proximal end of the proximal shaft section 72prox. This proximal T hub has a proximal Luer connector 80 and a side arm 82 having a female Luer connector that extends substantially perpendicular to the longitudinal axis of the hub 76, as shown. When compared to a typical Y hub, the side arm 82 of this T hub is further away from the proximal Luer connector 80 and is oriented at a right angle to the proximal Luer connector 80. Thus, tubing connected to this perpendicular side arm 82 is less likely to obscure or block the proximal Luer connector 80 than in a typical Y hub and the operator is less likely to confuse the proximal Luer connector 80 with the Luer connector on the side arm 82.

In various embodiments, the overall length of the catheter shaft 72 may be in the range of about 24 cm to about 30 cm and in one embodiment about 25 cm. The proximal shaft section 72prox may have a length in the range of about 9 cm to about 15 cm, and the distal shaft section 72dist may have a length in the range of about 5 cm to about 10 cm. In the embodiment shown in FIG. 12, the catheter shaft 72 has an effective length of 18.9 cm±0.3 cm, and an overall length of 20.0 cm±0.5 cm. Further, the proximal shaft section 72prox is 11.1 cm±0.2 cm in length and the distal shaft section 72dist has a flexible length of 7.75 cm±0.3 cm in length. The flexible length is measured from the proximal end of the distal shaft section to the distal shoulder 75dist of the balloon 74.

The "ineffective tip length" of the distal shaft section 72dist, from the distal shoulder 75dist of the balloon to the end of the distal tip member 78, is 1.1 cm±0.2 cm for a 7 mm balloon. For different balloon sizes, the ineffective tip length is 0.75 cm±0.2 cm for a 3.5 mm balloon, 0.9 cm±0.2 cm for a 5 mm balloon, and 1.0 cm±0.2 cm for a 6 mm balloon. Also, the distal tip member 78 is atraumatic and may have a radius shaped distal end.

Referring now to the cross sectional view of FIG. 12A, the proximal shaft section 72prox may include a rigid outer tube 90, a flexible middle tube 92 disposed substantially coaxially within the lumen of the rigid outer tube 90, and an inner tube 96 disposed substantially coaxially within the lumen of the middle tube 92. In this embodiment, the outer tube 90 is formed of stainless steel hypotube or support tube having an outer diameter of about 0.076 inches and an inner diameter of about 0.068 inches. The relatively larger outer diameter of outer tube 90 compared to the outer tube 30 of balloon catheter 10, helps decrease the inflation time of the balloon 74. As an alternative to stainless steel hypotube, this outer tube 90 may be formed of rigid non-metallic material such as polyetheretherketone (PEEK) or other rigid plastics suitable for such application. Alternatively, other rigid reinforcing members may be used in, or in lieu of, the outer tube, such as wires (round, flat, square or of other cross section), partial tubes (e.g., arcs), etc. Also, in this particular example, the middle tube 92 is formed of Pebax having an inner diameter of 0.055 inches, an outer diameter of 0.065+/−0.003 inches. The inner tube 96 is formed of polyether block copolymer tubing (e.g., Pebax® Resin, Arkema, Inc., Philadelphia, Pa.) having an inner diameter of at least 0.036 inches, and preferably having an inner diameter of 0.038 inches and an outer diameter of 0.048 inches. Having an inner tube 96 with an inner diameter of at least 0.036 inches allows the balloon catheter 70 to be compatible with multiple types of guidewires, including a lighted guidewire, such as the Acclarent Relieva Luma™ Sinus Illumination Guidewire, which has an outer diameter of 0.0354 inches.

The outer tube 90 terminates at the end of the proximal shaft section 72prox. The middle tube 92 and inner tube 96 extend beyond the distal end of the outer tube 90, forming the distal shaft section 72dist.

As seen in FIG. 12A, a polyether block copolymer film laminate 91 (e.g., Pebax® Resin, Arkema, Inc., Philadelphia, Pa.) is heat shrunk onto the outer surface of the catheter shaft 72 from the proximal hub 76 to the balloon 74. This laminate 91 provides a smooth outer surface and smoothes the step-down in diameter from the distal end of the proximal shaft section 72prox to the proximal end of the distal shaft section 72dist (i.e., it provides a smooth surface over the distal end of the outer tube 90 and the adjacent outer surface of the middle tube 92). The smooth step down may also be formed by an adhesive fillet. In other embodiments, the smooth step down may be formed by tapering or chamfering the structure of the distal end of the proximal shaft, eliminating the need for a laminate or adhesive.

The proximal end of the middle tube 92 extends into and is secured to the hub 76, distal to side arm Luer connector 82. The proximal end of the inner tube 96 extends into and is secured within hub 76, proximal to the side arm Luer connector 82 and in direct alignment and fluid communication with proximal Luer connector 80. The distal end of the middle tube 92 terminates within the balloon 74 and the proximal end of the dilator is secured to the outer surface of the middle tube. The distal end of the inner tube 96 also extends through the balloon 74 and protrudes distally beyond the balloon 74, forming the relatively flexible distal tip member 78 as shown in FIG. 12. The distal end of the balloon 74 is secured to the outer surface of the inner tube 96. In this manner, the inner tube lumen 98 extends through the entire catheter shaft 72 from the proximal Luer connector 80 through the distal tip 78 and may be used as a guidewire lumen or as a working lumen for infusion of irrigation solution, medicaments, contrast media or other substances and/or for aspiration of blood, fluids or debris. Guidewires that may be advantageously used in conjunction with this dilation catheter 70 may have a length of 60 cm to 80 cm and may be either 0.014 inch or 0.035 inch, such as those commercially available as the Relieva® Sinus Guidewires (Acclarent, Inc., Menlo Park, Calif.) or sizes in between such as 0.018 inch, 0.020 inch, or 0.033 inch. Although the drawings show an over-the-wire catheter having a guidewire lumen that extends through the entire length of the catheter, it is to be appreciated that guidewire lumens extending less than the entire length of the catheter (e.g., rapid exchange guidewire lumens) may be used as an alternative to the over-the-wire lumen shown. Additionally, in some embodiments, rather than advancing the catheter over a guidewire, the catheter may be equipped with a fixed guidewire tip such as any of those described in U.S. patent application Ser. No. 11/438,090, issued as U.S. Pat. No. 8,951,225 on Feb. 10, 2015, entitled Catheters with Non-Removable Guide Members Useable for Treatment of Sinusitis, the entire disclosure of which is expressly incorporated herein by reference.

The inner tube lumen 98 may be lined or coated with a lubricious material to facilitate passages of the guidewire GW through that lumen 98. The diameter of the inner tube 96 may be changed to accommodate guidewires of different diameter. In the particular embodiment described, the inner tube lumen 98 is sized to receive a 0.035 inch diameter guidewire GW. The inner tube lumen 98 may be internally lined or coated with a 2% solution of linear polydimethylsiloxane (PDMS) (e.g., Dow Corning® 360 Medical Fluid, Dow Corning Corporation, Midland, Mich.) diluted in isopropyl alcohol or another silicone material (such as a 2% solution of Dow-Corning MDX4-4159 in isopropyl alcohol). The coating is cured at room temperature.

The luminal space 94 between the outer surface of the inner tube 96 and the inner surface of the middle tube 92 is in fluidic communication with the side arm Luer connector 82 and extends to the interior of the balloon 74. Thus, this luminal space 94 serves as the passageway through which inflation fluid is passes into and out of the balloon 74. The size of this luminal space 94 and the relatively short length of the catheter shaft 72 are optimized to minimize drag on inflation fluid passing through this luminal space 94 and allows for rapid deflation of the balloon 74. The clearance of 0.006 to 0.007 inches between the inner and outer member is desired for catheter length of 20-35 cm. The desired deflation time is less than or equal to about 5 seconds and the deflation time is measured with application of negative pressure on the inflation/deflation lumen using a 20 cc inflation device that is filled with 10 cc contrast/saline mixture.

FIG. 12B shows details of the balloon 74. In this embodiment, the balloon 74 is a non-compliant balloon formed of polyethylene teraphthalate (PET) film having a thickness of 0.8 mils. The balloon 74 has a triangular or tri-fold (or approximately triangular) cross-sectional shape 104 in a partially inflated state. In alternative embodiments, the balloon 74 may have any suitable geometry in a partially inflated state, such as a round shape or any suitable non-round shape. The approximately triangular shape 104 may facilitate wrapping and/or re-wrapping the balloon 74 around the outer tube 90. In use, the triangular cross-sectional shape of the balloon allows the balloon, when deflated, to more easily re-wrap and pass back through the guide catheter for removal from a patient. Various balloon catheters 70 having variously sized balloons 74 may be provided, such as but not limited to the following sizes (diameter×effective length of the balloon in millimeters): 5×16, 6×16, 7×16, 5×24, 7×24, 3.5×12. Other balloon sizes may also be available. The working length (or "effective length") of the balloon is measured from a proximal shoulder 75prox to a distal shoulder 75dist of the balloon 74. In some embodiments, a number of catheters having a number of balloon sizes may be provided to a user, so that the physician user may choose one or more sizes based on the anatomy to be treated, physician preference and/or the like. In one embodiment, the balloon 74 may have a rated burst pressure of at least about 10 to about 16 atmospheres and preferably about 14 to about 16 atmospheres.

The balloon 74 also includes tapered proximal and distal end regions 106prox and 106dist. In some embodiments, each of the two tapered end regions 106prox, 106dist may have the same length. This length of the tapered regions 106prox, 106dist may be different for differently sized balloons 74. For example, in one set of balloon 74 embodiments, a balloon 74 having a diameter of at about 7 mm may have a taper length of about 6 mm, a balloon 74 having a diameter of at about 6 mm may have a taper length of about 5 mm, a balloon 74 having a diameter of at about 5 mm may have a taper length of about 4 mm, and a balloon 74 having a diameter of at about 3.5 mm may have a taper length of about 2.5 mm.

The tapered end regions 106prox, 106dist are tapered at angle A relative to the longitudinal axis LA of the catheter shaft 72 on which the balloon 74 is mounted. This angle of taper A may be in the range of about 10 degrees to about 30 degrees. In the particular example shown in the drawings, such angle of taper A is 20 degrees. This 20 degree angle of taper provides improved transition from balloon working length to the necks, lower profile, improved crossing, improved track, easier withdrawal in the sinus guide after balloon deflation. It also provides optimal performance with minimum increase of overall balloon length.

As best shown in FIG. 12B, the balloon 74 includes an extended balloon neck 77. In this embodiment, the balloon neck is about 1 cm in length. A proximal end of the balloon neck 77 may be bonded to the distal shaft portion 72dist. The extended balloon neck provides a separation between the bond to the shaft 72 and the tapered end region 106prox. This separation allows a marker to be disposed on the shaft and aligned with the proximal end of the balloon (at the proximal taper) without being disposed on or near the bond (adhesive) that secures the balloon to the shaft.

As shown in FIGS. 12 and 12B, in some embodiments, direct visualization markers and/or radiographic markers may be disposed along the catheter shaft 72. Generally, "direct visualization markers" refers to markers that may be viewed during use with the naked eye or by use of an endoscope, while radiographic markers include radiopaque material and are viewed using a radiographic device such as infra-operative fluoroscopy. In one embodiment, at the distal end, there is a first distal radiographic marker 110a, which has a proximal edge aligned with the location where the proximal taper 106prox meets the effective length of the balloon 74. There is also a second distal radiographic marker 110b, which has a distal edge aligned with the location where the distal taper 106distal meets the effective length of the balloon 74. The distance across the outside edges of the distal markers 110a and 110b is about 1.6 cm±0.2 cm and represents the effective length of the balloon 74. The distal markers 110a and 110b may be platinum marker bands. In this embodiment, the distal markers help to ensure that the balloon catheter 70 is in a straight position inside the guide during the device loading and preparation.

Direct visualization markers can be positioned in a number of locations along the catheter shaft 72. Although one embodiment is described here with reference to FIGS. 12 and 12B, other variations may be substituted in alternative embodiments. In one embodiment, shaft 72 may have a dark color, such as black, dark blue, dark grey or the like, and markers may have a light color, such as white, green, red or the like. In some embodiments, markers may have different colors and/or different widths to facilitate distinguishing the markers from one another during use. This contrast in colors may facilitate viewing the markers in a darkened operation room and/or when using an endoscope inside a patient in the presence of blood.

In one embodiment, there may be a first distal shaft marker 112 (or "endoscopic marker," since it is typically viewed during use via an endoscope) disposed on the shaft 72 at a location such that its distal edge aligns with the location where the proximal taper of the balloon 74 meets the catheter shaft 72. The extended balloon neck 77 allows the first endoscopic marker 112 to be placed on the shaft and away from any adhesive bonding used to secure the proximal end of the balloon neck to the shaft. The first endoscopic marker 112 indicates to the user the ending location of the balloon 74 and indicates that the balloon has exited the guide during a procedure. In one embodiment, the first endoscopic marker 112 may be about 2 mm wide.

A second distal shaft marker 114 is disposed on the shaft 72 such that the distal edge of the marker is 1 cm±0.2 cm from the location where the proximal taper of the balloon 74 meets the catheter shaft 72. This marker indicates to the user that the shaft location is 1 cm away from the end of the balloon indicating that the balloon has extended from the guide during the procedure. In one embodiment, the second distal shaft marker may be about 2 mm wide and white in color, while the first marker is about 2 mm and green in color. Of course, any of a number of different size and color combinations may be used alternatively.

A third distal shaft marker 116 is disposed on the shaft 72 such that the distal edge of the marker is 1 cm±0.1 cm from the distal edge of the second distal shaft marker 114. As shown in FIG. 12B, the third distal shaft marker is a double marker to distinguish the second and third distal shaft markers 114 and 116 from one another. The third distal shaft marker 116 indicates the shaft location 2 cm away from the end proximal end of the balloon 74, thus indicating the distance the balloon has extended from the guide during the procedure. In one embodiment, the two markers forming the third distal shaft marker 116 are each 0.75 mm wide and white in color, however, the size and color of the marker can be changed in alternative embodiments. The differences in the first, second and third distal shaft markers' color, length and number of marks give the indication of the relative location proximal to the balloon under endoscopic visibility. Using an endoscope, the physician user can identify the length of catheter that has been advanced and retracted out of a guide catheter and/or can approximate a location of the balloon 74 relative to patient anatomy such as a paranasal sinus ostium, other paranasal sinus opening, or other openings in the ear, nose or throat. This approximation of balloon position may be very useful in circumstances when the balloon 74 has been advanced far enough into an anatomical location that the balloon 74 can no longer be viewed via endoscope. For example, using the three endoscopic markers, the user is able to endoscopically gauge the distance the catheter has advanced into the frontal recess once the proximal portion of the balloon is no longer visible. Of course, in alternative embodiments, distal shaft markers having different numbers, sizes, colors and positions along the catheter shaft may be used.

In some embodiments, in addition to one or more distal shaft markers, one or more proximal shaft markers may be disposed along the proximal portion of catheter shaft 72. In general, such proximal shaft markers may be viewed directly by a physician, without using an endoscope, to indicate to the physician a location of the balloon 74 of the catheter 70 relative to a guide catheter through which the balloon catheter 70 is being advanced. As with the distal shaft markers, the proximal shaft markers may have any suitable width, color, number, position and the like. In one embodiment, for example, as shown in FIG. 12, two proximal shaft markers 118, 120 may have a light color to contrast with a dark colored shaft 72 and increase visibility in a darkened operating room. The more proximal of the proximal markers 118 (or the "first proximal shaft marker") may indicate that a tip of the balloon catheter 74 is at a distal end of the guide catheter and that the balloon 74 has exited the distal end of the guide catheter as the marker 118 passes into the proximal end of the guide catheter. The more distal of the proximal markers 120 (or the "second proximal shaft marker") may indicate to a user that the balloon 74 is just proximal to a curve in a guide catheter when marker 120 is located at the proximal end of the guide catheter.

In one embodiment, the first proximal shaft marker 118 is disposed on the shaft 72 such that the length from the proximal end of the proximal balloon taper 106 to the proximal end of the first shaft marker is 13.1 cm±0.2 cm. The first proximal shaft marker is 4.1 cm±0.1 cm in length for a 7×24 mm balloon catheter. The length of the first proximal shaft marker 118 can vary depending on the size of the balloon catheter. The length of the first proximal shaft marker 118 may be determined by adding the length of the distal tip 78, the effective or working length of the balloon 74, and the lengths of the two balloon taper sections. Also, the first proximal shaft marker is preferably white in color, however, other light colors, such as grey, can be used as well.

The second proximal shaft marker 120 is disposed on the shaft 72 distally from the first proximal shaft marker 118. The second proximal shaft marker 120 is positioned such that the distal tip of the catheter 70 is 11.4 cm±0.2 cm from the distal edge of the second proximal shaft marker 120. Also, the second proximal shaft marker 120 has a length of 3 mm±2 mm. It is preferred that the second shaft proximal marker 120 is white in color, however, other light colors, such as grey, can be used as well.

When the balloon catheter 70 is inserted into a guide, a user may visualize the first and second proximal shaft markers 118 and 120 to determine the position of the distal tip and the balloon 74 of the balloon catheter 70 relative to the sinus guide catheter. For instance, when the second proximal shaft marker 120 is aligned with the proximal opening of the guide catheter, the user will know that the balloon 74 is proximal to the curve of the guide catheter. The position of the second proximal shaft marker 120 helps to visually ensure that the balloon catheter 70 is properly loaded into the sinus guide catheter. When the distal edge of the first proximal shaft marker 118 is aligned with the proximal opening of the guide catheter, the user knows that the distal tip of the balloon catheter 70 is beginning to exit the guide catheter, and when the proximal edge of the first proximal shaft marker is aligned with the proximal opening of the guide catheter, the user knows that the balloon is completely out of the guide catheter.

The visible markers 114, 116, 118 and 120 are preferably light in color, such as white as indicated above, to contrast with a dark color of the shaft 72, which is preferably black. The high contrast between these visible markers and the shaft helps view the markers in a low light environment. Also, the high contrast allows the user to view directly with an endoscope the markers and know where the balloon 74 is located relative to a sinus ostium. Furthermore, the color contrast is useful during the procedure when the field is full of blood and/or mucus to view the markers and know the position of the balloon.

The alternative embodiment of the balloon catheter 70 is used in a similar manner to the first embodiment of the balloon catheter 10 as described above. Further, separate features of the balloon catheters 10 and 70 may be incorporated into or used with either embodiment.

The invention has been described with reference to certain examples or embodiments of the invention, but various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A system for dilating an opening in a paranasal sinus, the system comprising:
   (a) a guide catheter comprising a proximal end and a distal end; and
   (b) a balloon dilation catheter configured to be advanced through the guide catheter, the balloon dilation catheter comprising:
      (i) a catheter shaft having:
         (A) a longitudinal axis,
         (B) an inflation lumen,
         (C) a distal end,
         (D) a proximal end,
         (E) a proximal shaft section, wherein the proximal shaft section comprises:
            (1) an outer tube,
            (2) an inner tube within the outer tube, wherein the inner tube includes an inflation lumen, and
            (3) a middle tube between the inner tube and the outer tube, and
         (F) a distal shaft section, wherein the distal shaft section comprises:
            (1) a distal portion of the middle tube, and
            (2) a distal portion of the inner tube, and
         (G) a tapered section between the proximal shaft section and the distal shaft section,
      (ii) an inflatable balloon disposed on the distal shaft section in fluid communication with the inflation lumen, wherein a distal end of the middle tube terminates within the inflatable balloon and the proximal end of the inflatable balloon is secured to the outer surface of the middle tube,
      (iii) a first proximal shaft marker disposed on the proximal shaft section and having a lighter color than the catheter shaft, wherein the first proximal shaft marker is configured to be visualized directly at a location proximal to the proximal end of the guide catheter to allow a user to approximate a position of the balloon relative to the guide catheter, and
      (iv) a first distal shaft marker disposed on the distal shaft section proximal to a proximal end of the balloon and having a lighter color than the catheter shaft.

2. The system of claim 1, further comprising a second proximal shaft marker disposed on the proximal shaft section distally from the first proximal shaft marker and having a lighter color than the catheter shaft, wherein the first shaft marker has a greater length than the second shaft marker.

3. The system of claim 2, wherein the length of the first proximal shaft marker is equal to a length from a proximal end of the balloon to the distal end of the catheter shaft, wherein the first shaft marker is spaced from the distal end of the catheter shaft such that it allows the user to approximate when the distal end of the shaft is located at the distal end of the guide catheter and when the proximal end of the balloon exits the guide catheter, and wherein the second proximal shaft marker allows the user to approximate when the distal end of the catheter shaft is located just proximal to a curve in the guide catheter.

4. The system of claim 1, further comprising a second distal shaft marker disposed on the distal shaft section proximal to the first distal shaft marker and having a lighter color than the catheter shaft.

5. The system of claim 4, wherein the first distal shaft marker is disposed at a known distance proximally from the proximal end of the balloon, and the second distal shaft marker is disposed at a known distance proximally from the first distal shaft marker, and wherein the first and second distal shaft marker have different appearances.

6. The system of claim 5, wherein the first distal shaft marker is disposed approximately one centimeter from the proximal end of the balloon and the second distal shaft marker is disposed approximately two centimeters from the proximal end of the balloon.

7. The system of claim 4, further comprising a third distal shaft marker disposed on the distal shaft section at the proximal end of the balloon.

8. The system of claim 1, further comprising:
(a) a first radiopaque marker disposed on the distal shaft section within the balloon; and
(b) a second radiopaque marker disposed on the distal shaft section distally from the first radiopaque marker within the balloon;
wherein the first and second radiopaque markers are disposed a distance apart from one another to indicate the effective length of the balloon.

9. The system of claim 1, wherein the balloon further comprises an approximately triangular cross-sectional shape in a partially inflated state.

10. The system of claim 1, wherein the balloon further comprises a balloon neck extending from the balloon and proximally along the catheter shaft.

11. The system of claim 10, wherein the first proximal shaft marker is disposed on the distal shaft section and underneath the balloon neck.

12. The system of claim 1, wherein the balloon dilation catheter further comprises a guidewire lumen.

13. The system of claim 1, further comprising a guidewire that is advanceable through the guidewire lumen.

14. The system of claim 1, wherein the inflation fluid lumen is sized so that, after the balloon has been inflated to a working diameter, the balloon will deflate in less than 5 seconds with application of negative pressure to the inflation fluid lumen by a conventional balloon catheter inflation and deflation device.

15. The system of claim 1, further comprising an irrigation catheter sized for advancement through the guide catheter into a paranasal sinus.

16. The system of claim 1, wherein the guide catheter further comprises an anti-reflective coating or treatment.

17. The system of claim 1, wherein the balloon dilation catheter further comprises an anti-reflective coating or treatment.

18. A system for dilating an opening in a paranasal sinus, the system comprising:
(a) a guide catheter comprising a proximal end and a distal end; and
(b) a balloon dilation catheter configured to be advanced through the guide catheter, the balloon dilation catheter comprising:
  (i) a catheter shaft having:
    (A) a longitudinal axis,
    (B) an inflation lumen,
    (C) a distal end,
    (D) a proximal end,
    (E) a proximal shaft section, wherein the proximal shaft section comprises:
      (1) an outer tube,
      (2) an inner tube within the outer tube, wherein the inner tube includes an inflation lumen, and
      (3) a middle tube between the inner tube and the outer tube, and
    (F) a distal shaft section, wherein the distal shaft section comprises:
      (1) a distal portion of the middle tube, and
      (2) a distal portion of the inner tube, and
    (G) a tapered section between the proximal shaft section and the distal shaft section,
  (ii) an inflatable balloon disposed on the distal shaft section in fluid communication with the inflation lumen, wherein a distal end of the middle tube terminates within the inflatable balloon and the proximal end of the inflatable balloon is secured to the outer surface of the middle tube,
  (iii) a first proximal shaft marker disposed on the proximal shaft section and having a lighter color than the catheter shaft, wherein the first proximal shaft marker is configured to be visualized directly at a location proximal to the proximal end of the guide catheter to allow a user to approximate a position of the balloon relative to the guide catheter, and
  (iv) a first distal shaft marker disposed on the distal shaft section proximal to a proximal end of the balloon and having a lighter color than the catheter shaft, wherein high contrast between the first proximal and distal shaft markers and the catheter shaft allows for viewing of the first proximal and distal shaft markers in a low light environment.

19. The system of claim 18, further comprising an endoscope configured to provide endoscopic visualization of the first distal shaft marker to enable a user to approximate a position of the balloon relative to an opening of a paranasal sinus.

20. A method of operating a dilation system, the system comprising:
(a) a guide catheter comprising a proximal end and a distal end; and
(b) a balloon dilation catheter configured to be advanced through the guide catheter, the balloon dilation catheter comprising:
  (i) a catheter shaft having a longitudinal axis, an inflation lumen, a distal end, a proximal end, a proximal shaft section that is substantially rigid, and a distal shaft section that is more flexible than the proximal shaft section, wherein the catheter shaft is dark in color,
  (ii) an inflatable balloon disposed on the distal shaft section in fluid communication with the inflation lumen,
  (iii) a first proximal shaft marker disposed on the proximal shaft section and having a lighter color than the catheter shaft, and
  (iv) a first distal shaft marker disposed on the distal shaft section proximal to a proximal end of the balloon and having a lighter color than the catheter shaft,
wherein the method comprises:
(a) inserting the guide catheter into a nostril of the patient;
(b) advancing the guide catheter near a passageway of a paranasal sinus;
(c) advancing the balloon dilation catheter through the guide catheter;
(d) directly visualizing the first proximal shaft marker at a location proximal relative to the proximal end of the guide catheter to approximate a position of the balloon relative to the guide catheter; and
(e) endoscopically visualizing the first distal shaft marker relative to a passageway of the paranasal sinus.

* * * * *